(12) United States Patent
Metzger et al.

(10) Patent No.: US 12,410,111 B2
(45) Date of Patent: Sep. 9, 2025

(54) PROCESSES FOR CONVERTING C8 AROMATIC HYDROCARBONS

(71) Applicant: ExxonMobil Chemical Patents Inc., Baytown, TX (US)

(72) Inventors: Eric D. Metzger, Houston, TX (US); Mayank Shekhar, Houston, TX (US); Wenyih F. Lai, Bridgewater, NJ (US); Paul Podsiadlo, Spring, TX (US); Dominick A. Zurlo, Easton, PA (US); Kathleen M. Keville, Beaumont, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 249 days.

(21) Appl. No.: 17/996,007

(22) PCT Filed: Mar. 12, 2021

(86) PCT No.: PCT/US2021/022241
§ 371 (c)(1),
(2) Date: Oct. 12, 2022

(87) PCT Pub. No.: WO2021/211240
PCT Pub. Date: Oct. 21, 2021

(65) Prior Publication Data
US 2023/0212094 A1    Jul. 6, 2023

Related U.S. Application Data

(60) Provisional application No. 63/011,436, filed on Apr. 17, 2020.

(30) Foreign Application Priority Data

Jun. 11, 2020   (EP) .................................... 20179410

(51) Int. Cl.
*B01J 29/40*   (2006.01)
*B01J 29/80*   (2006.01)
(Continued)

(52) U.S. Cl.
CPC ............. *C07C 5/2737* (2013.01); *B01J 29/40* (2013.01); *B01J 29/80* (2013.01); *B01J 35/393* (2024.01);
(Continued)

(58) Field of Classification Search
CPC ..... C07C 5/2737; C07C 4/18; C07C 2529/40; C07C 2529/80; C07C 5/222; B01J 29/40;
(Continued)

(56) References Cited

U.S. PATENT DOCUMENTS 3,090,691 A    5/1963   Weyer
3,354,078 A   11/1967   Miale et al.
(Continued)

FOREIGN PATENT DOCUMENTS

CN   103418422 B      6/2016
WO   2002/088056 A1  11/2002
WO   2021/211240 A1  10/2021

OTHER PUBLICATIONS

Extended European Search Report received for European Patent Application No. 20179410.4 mailed on Nov. 11, 2020, 6 Pages.
(Continued)

*Primary Examiner* — Prem C Singh
*Assistant Examiner* — Francis C Campanell
(74) *Attorney, Agent, or Firm* — ExxonMobil Technology and Engineering Company (57) ABSTRACT

Processes for converting C8 aromatic hydrocarbons. In some embodiments, the process can include feeding a gaseous hydrocarbon feed that can include meta-xylene, ortho-xylene, or both into a conversion zone. The process can also
(Continued)

include contacting the gaseous hydrocarbon feed with a catalyst that can include a ZSM-11 zeolite in the conversion zone under conversion conditions to effect isomerization of at least a portion of any meta-xylene, or at least a portion of any ortho-xylene, or both to produce a conversion product rich in para-xylene. In some embodiments, the ZSM-11 zeolite can have an alpha value of 1 to 3,000 and a molar ratio of silica to alumina of from 15 to 200.

16 Claims, 3 Drawing Sheets

(51) Int. Cl.
*B01J 35/30* (2024.01)
*B01J 35/61* (2024.01)
*C07C 4/18* (2006.01)
*C07C 5/27* (2006.01)

(52) U.S. Cl.
CPC ........... *B01J 35/613* (2024.01); *B01J 35/615* (2024.01); *B01J 35/617* (2024.01); *C07C 4/18* (2013.01); *C07C 2529/40* (2013.01); *C07C 2529/80* (2013.01)

(58) Field of Classification Search
CPC ........ B01J 29/80; B01J 35/393; B01J 35/613; B01J 35/615; B01J 35/617; B01J 2235/00; B01J 2235/15; B01J 2235/30; Y02P 20/52
USPC .......................................................... 585/321
See application file for complete search history.

(56) References Cited

U.S. PATENT DOCUMENTS

| | | |
|---|---|---|
| 3,702,886 A | 11/1972 | Argauer et al. |
| 3,709,979 A | 1/1973 | Chu |
| 3,832,449 A | 8/1974 | Rosinski et al. |
| 4,016,245 A | 4/1977 | Plank et al. |
| 4,076,842 A | 2/1978 | Plank et al. |
| 4,117,026 A | 9/1978 | Haag et al. |
| RE29,948 E | 3/1979 | Dwyer et al. |
| 4,397,827 A | 8/1983 | Chu |
| 4,417,780 A | 11/1983 | Knapp |
| 4,526,879 A | 7/1985 | Dwyer et al. |
| 4,556,477 A | 12/1985 | Dwyer |
| 4,582,815 A | 4/1986 | Bowes |
| 4,631,267 A | 12/1986 | Lachman et al. |
| 4,899,011 A | 2/1990 | Chu et al. |
| 5,053,374 A | 10/1991 | Absil et al. |
| 5,182,242 A | 1/1993 | Marler |
| 5,476,823 A | 12/1995 | Beck et al. |
| 5,689,027 A | 11/1997 | Abichandani et al. |
| 5,977,420 A | 11/1999 | Abichandani et al. |
| 6,277,355 B1* | 8/2001 | Kennedy ................. C01B 39/40 423/DIG. 22 |
| 7,247,762 B2 | 7/2007 | Stern |
| 7,271,118 B2 | 9/2007 | Raich et al. |
| 8,273,934 B2 | 9/2012 | Ou et al. |
| 2010/0048381 A1* | 2/2010 | Oh .......................... B01J 29/076 502/66 |
| 2013/0217936 A1 | 8/2013 | Cheng et al. |
| 2016/0221832 A1* | 8/2016 | Lai ........................... C01B 39/26 |

OTHER PUBLICATIONS

Miale, J. et al., (1966) "Catalysis by crystalline aluminosilicates: IV. Attainable catalytic cracking rate constants, and superactivity.", Journal of Catalysis, vol. 6, No. 2, pp. 278-287.

Millward, G. R. et al., (1983) "Evidence for semi-regularly ordered sequences of mirror and inversion symmetry planes in ZSM-5/ZSM-11 shape-selective zeolitic catalysts.", Journal of the Chemical Society, Faraday Transactions 2: Molecular and Chemical Physics, vol. 79, No. 7, pp. 1075-1082.

Olson, D. H. et al., (1980) "Chemical and Physical Properties of the ZSM-5 Substitutional Series", Journal of Catalysis, vol. 61, No. 2, pp. 390-396.

International Preliminary Report on Patentability received for PCT Application No. PCT/US2021/022241, mailed on Oct. 27, 2022, 8 Pages.

International Search Report and Written Opinion received for PCT Application No. PCT/US2021/022241, mailing date on May 18, 2021, 10 Pages.

Wang, X. et al., (2017) "Synthesis of a hierarchical ZSM-11/5 composite zeolite of high SiO2/Al2O3 ratio and catalytic performance in the methanol-to-olefins reaction", Comptes Rendus Chimie, vol. 20, No. 11-12, pp. 1083-1092.

Periodic Table of Elements as described in Chemical and Engineering News, 63(5), p. 27 (1985).

G. A. Jablonski, L. B. Sand, and J. A. Gard, Zeolites, vol. 6, Issue 5, pp. 396-402 (1986).

Journal of Catalysis, vol. 4, p. 527 (1965).

* cited by examiner

PROCESSES FOR CONVERTING C8 AROMATIC HYDROCARBONS

CROSS-REFERENCE TO RELATED APPLICATIONS

This application is a U.S. national phase application of PCT Application Serial No. PCT/US2021/022241 having a filing date of Mar. 12, 2021, which claims priority to and the benefit of U.S. Provisional Application No. 63/011,436, filed Apr. 17, 2020 and EP Application Serial No. 20179410.4, filed Jun. 11, 2020, the disclosures of which are incorporated herein by reference in their entirety.

FIELD

This disclosure relates to processes for converting C8 aromatic hydrocarbons. More particularly, this disclosure relates to processes for vapor phase isomerization of meta-xylene and/or ortho-xylene to produce para-xylene.

BACKGROUND

Catalytically reforming a hydrocarbon feed such as naphtha using conventional aromatization catalysts produces a reformate that is richer in C6-C10 aromatics than the hydrocarbon feed. Of these aromatics, significant quantities of C8 aromatics are produced that include a mixture of ethylbenzene and mixed meta-, ortho-, and para-xylene isomers. Typically, the product (reformate) from the catalytic reformer is fed to an aromatic extraction plant where the aromatics, e.g., C6, C7, and C8 aromatics, are separated from the paraffins and other non-aromatic compounds present in the reformate. The C8 aromatic fraction can then be separated from the lower boiling C6 and C7 aromatics, e.g., via distillation.

The three xylene isomers in the C8 aromatic fraction are usually present in near thermodynamically equilibrium amounts, i.e., generally 52 wt % to 53 wt % of meta-xylene, 23.5 wt % to 24.5 wt % of ortho-xylene, and 23 wt % to 24 wt % of para-xylene. Para-xylene is a more valuable isomer because it is used as a chemical intermediate in a number of applications and it may be desirable to separate the para-xylene from the other isomers using conventional techniques such as crystallization and/or by adsorption/desorption on zeolites. After such separation, the residual C8 aromatic fraction can include non-equilibrium quantities of the meta- and ortho-xylene isomers and can be lean with respect to para-xylene content.

The residual C8 aromatic fraction can be further upgraded by subjecting it to conversion conditions where at least a portion of the ortho-xylene and/or the meta-xylene undergoes isomerization to produce a mixture that can approximate the equilibrium concentration of the meta-, ortho-, and para-xylene isomers. Current vapor phase isomerization processes undergo xylenes loss, e.g., conversion to methylbenzene and A9+ compounds, and could benefit from a reduction in xylenes loss and/or an increased weight hourly space velocity during isomerization.

There is a need, therefore, for improved processes for vapor phase xylene isomerization. This disclosure satisfies this and other needs.

SUMMARY

Processes for converting C8 aromatic hydrocarbons are provided. In some embodiments, the process can include feeding a gaseous hydrocarbon feed that can include meta-xylene, ortho-xylene, or both into a conversion zone. The gaseous hydrocarbon feed can be contacted with a catalyst that can include a ZSM-11 zeolite in the conversion zone under conversion conditions to effect isomerization of at least a portion of any meta-xylene, at least a portion of any ortho-xylene, or both to produce a conversion product rich in para-xylene. In some embodiments, the ZSM-11 zeolite can have an alpha value of 1 to 3,000 and a silica to alumina molar ratio of from 15 to 200.

In other embodiments, the process can include feeding a gaseous hydrocarbon feed that can include ethylbenzene and at least one of ortho-xylene and meta-xylene into a first conversion zone. The gaseous hydrocarbon feed can be contacted with a first catalyst in the first conversion zone under first conversion conditions to effect conversion of at least a portion of the ethylbenzene into benzene and ethane to produce a gaseous effluent lean in ethylbenzene. The process can also include feeding the gaseous effluent into a second conversion zone. The gaseous effluent can be contacted with a second catalyst that can include a ZSM-11 zeolite within the second conversion zone under second conversion conditions to effect isomerization of at least a portion of any ortho-xylene, at least a portion of any meta-xylene, or both to para-xylene to produce a conversion product rich in para-xylene. In some embodiments, the ZSM-11 zeolite can have an alpha value of 1 to 3,000 and a silica to alumina molar ratio of from 15 to 200.

DETAILED DESCRIPTION

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

The indefinite article "a" or "an", as used herein, means "at least one" unless specified to the contrary or the context clearly indicates otherwise. Thus, embodiments using "a reactor" or "a conversion zone" include embodiments where one, two or more reactors or conversion zones are used, unless specified to the contrary or the context clearly indicates that only one reactor or conversion zone is used.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, ..., Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn-hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

"Crystal" means a crystalline material. Crystals can be observed using microscopes such as transmission electron microscope ("TEM"), scanning electron microscope ("SEM"), reflection electron microscope ("REM"), scanning transmission electron microscope ("STEM"), and the like. Single crystals can aggregate to form a polycrystalline material.

For the purposes of this disclosure, the nomenclature of elements is pursuant to the version of Periodic Table of Elements as described in CHEMICAL AND ENGINEERING NEWS, 63(5), pg. 27 (1985).

The term "rich" when used in phrases such as "X-rich" or "rich in X" means, with respect to an outgoing stream obtained from a device, e.g., a conversion zone, that the stream comprises material X at a concentration higher than in the feed material fed to the same device from which the stream is derived. The term "lean" when used in phrases such as "X-lean" or "lean in X" means, with respect to an outgoing stream obtained from a device, e.g., a conversion zone, that the stream comprises material X at a concentration lower than in the feed material fed to the same device from which the stream is derived.

The terms "para-xylene selectivity" and "pX selectivity" are used interchangeably and refer to the para-xylene concentration among all xylenes in a conversion product or conversion product rich in para-xylene.

The term "comparable para-xylene selectivity" means the para-xylene selectivity for each of two given examples is within about 2 percent of one another. For example, a first product that has a para-xylene selectivity of 20% would have a comparable para-xylene selectivity relative to a second product that has a para-xylene selectivity of +/−0.4%, i.e., 19.6% to 20.4%.

The term "comparable ethylbenzene conversion" means the conversion of ethylbenzene for each of two given examples is within about 10 percentage points or less of one another. For example, a first product that has an ethylbenzene conversion of 60% would have a comparable ethylbenzene conversion relative to a second product that has an ethylbenzene conversion of +/−5%, i.e., 55% to 65%.

The term "xylenes loss" ("Lx(1)") can be calculated as $Lx(1)=100\%*(W1-W2)/W1$, where W1 is the aggregate weight of all xylenes present in the gaseous hydrocarbon feed that includes C8 aromatics, and W2 is the aggregate weight of all xylenes present in the conversion product.

The term "alpha value" refers to a measure of the cracking activity of a catalyst and is described in U.S. Pat. No. 3,354,078 and in the Journal of Catalysis, Vol. 4, p. 527 (1965); Vol. 6, p. 278 (1966) and the Journal of Catalysis, Vol. 61, p. 395 (1980). The alpha value can be measured at a temperature of 538° C. and a variable flow rate as described in the Journal of Catalysis, Vol. 61, p. 395 (1980).

The terms "micropore", "mesopore", and "macropore" refer to pores having an average cross-sectional length (diameter if circular) of less than 2 nm, from 2 nm to 50 nm, and greater than 50 nm, respectively.

The term "micropore surface area" refers to the surface area of a given sample attributable to pores having an average cross-sectional length (diameter if circular) of less than 2 nm. The term "mesopore surface area" refers to the surface area of a given sample attributable to pores having an average cross-sectional length (diameter if circular) of 2 nm to 50 nm. The term "macropore surface area" refers to the surface area of a given sample attributable to pores having an average cross-sectional length (diameter if circular) of greater than 50 nm.

The term "external surface area" is the total surface area of a given sample minus the micropore surface area of that sample and, as such, is equal to the sum of the mesopore surface area and the macropore surface area.

Overview

In some embodiments, a gaseous hydrocarbon feed that includes C8 aromatic hydrocarbons, e.g., meta-xylene and/or ortho-xylene, can be contacted with a catalyst that includes a ZSM-11 zeolite within a conversion zone under conversion conditions to effect isomerization of at least a portion of any meta-xylene, at least a portion of any ortho-xylene, or both to produce a conversion product rich in para-xylene. It has been surprisingly and unexpectedly discovered that by replacing a conventional catalyst, i.e., a catalyst that includes a ZSM-5 zeolite, with a catalyst that includes the ZSM-11 zeolite, a significant increase in the para-xylene selectivity in the conversion product and/or a significant decrease in xylenes loss can be obtained while significantly increasing the weight hour space velocity (WHSV), e.g., double the WHSV, as compared to the conventional catalyst when operated at comparable ethylbenzene conversion in a single conversion zone arrangement.

In other embodiments, the gaseous hydrocarbon feed that includes the C8 aromatic hydrocarbons, e.g., ethylbenzene and meta-xylene and/or ortho-xylene, can be contacted with the first catalyst in a first conversion zone under first conversion zone conditions to effect conversion of at least a portion of the ethylbenzene into benzene and ethane to produce an effluent lean in ethylbenzene. The effluent lean in ethylbenzene can be contacted with the second catalyst in a second conversion zone under second conversion zone conditions to effect isomerization of at least a portion of any meta-xylene, at least a portion of any ortho-xylene, or both to produce a conversion product rich in para-xylene.

It has also been surprisingly and unexpectedly discovered that by replacing the conventional second catalyst, i.e., a catalyst that includes a ZSM-5 zeolite, disposed within the second conversion zone with a second catalyst that includes the ZSM-11 zeolite, a significant increase in para-xylene selectivity in the conversion product and/or a significant decrease in xylene loses can be obtained while significantly increasing the weight hour space velocity (WHSV), e.g., double the WHSV, as compared to the conventional second catalyst when operated at comparable ethylbenzene conversion in a dual conversion zone arrangement. It has also been surprisingly and unexpectedly discovered that replacing the second conventional catalyst that includes the ZSM-5 zeolite with the catalyst that includes the ZSM-11 zeolite, when operating at a comparable xylene selectivity and comparable ethylbenzene conversion, the xylene losses attributable to the production of trimethylbenzenes can be reduced by 3%, 5%, 7%, 10%, 15%, 20%, 25%, 30%, 35%, 40%, 45%, 50%, or more.

ZSM-11 Zeolite

The catalyst that includes the ZSM-11 zeolite can include 1 wt %, 5 wt %, 10 wt %, 20 wt %, 30 wt %, or 40 wt % to 60 wt %, 70 wt %, 80 wt %, 90 wt %, or 100 wt % of the ZSM-11 zeolite, based on a total weight of the catalyst. The ZSM-11 zeolite can have an alpha value of 1, 10, 25, 50, 75, 100, 200, 300, or 400 to 500, 600, 700, 800, 900, 1,000, 1,250, 1,500, 1,750, 2,000, 2,250, 2,500, 2,750, or 3,000. In some embodiments, the ZSM-11 zeolite can have an alpha value of 1 to 3,000, 20 to 2,000, 20 to 1,000, or 25 to 750.

The ZSM-11 zeolite can have a silica ($SiO_2$) to alumina ($Al_2O_3$) molar ratio of from 15, 17.5, 20, 25, 30, 35, or 40 to 50, 75, 100, 125, 150, 175, or 200. In some embodiments, the ZSM-11 zeolite can have a silica to alumina molar ratio of from 15 to 200, 15 to 150, 15 to 100, 15 to 75, 15 to 50, 20 to 200, 20 to 150, 20 to 100, 20 to 75, 20 to 50, 30:200, 30 to 150, 30 to 100, 30 to 75, or 30 to 50. The silica to alumina molar ratio refers to the molar ratio in the rigid anionic framework of the zeolite and excludes any silicon (silicon metal and/or silica) and aluminum (aluminum metal and/or alumina) in a binder, e.g., when the zeolite is included as a component of an extrudate, or in cationic or other form within the channels of the zeolite. The silica to alumina molar ratio can be determined by conventional analysis, e.g., inductively coupled plasma mass spectrometry (ICP-MS) or X-ray fluorescence (XRF).

In some embodiments, the ZSM-11 zeolite can have an alpha value of 1 to 3,000, 20 to 2,000, 20 to 1,000, or 25 to 750 and a silica to alumina molar ratio of from 15 to 200, 15 to 150, 15 to 100, 15 to 75, 15 to 50, 20 to 200, 20 to 150, 20 to 100, 20 to 75, 20 to 50, 30:200, 30 to 150, 30 to 100, 30 to 75, or 30 to 50. In other embodiments, the ZSM-11 zeolite can have an alpha value of 1 to 3,000, 20 to 2,000, 20 to 1000, or 25 to 750 and a silica to alumina molar ratio of at least 15, at least 20, at least 25, at least 30, at least 35, at least 40, at least 45, or at least 50 to 75, 100, 150, or 200.

The ZSM-11 zeolite can have a total surface area of from 100 $m^2/g$, 150 $m^2/g$, 250 $m^2/g$, or 300 $m^2/g$ to 650 $m^2/g$, 700 $m^2/g$, 800 $m^2/g$, or 850 $m^2/g$. In some embodiments, the ZSM-11 zeolite can have a total surface area of from 100 $m^2/g$ to 800 $m^2/g$, 250 $m^2/g$ to 700 $m^2/g$, or 300 $m^2/g$ to 650 $m^2/g$.

The ZSM-11 zeolite can have a micropore surface area of from 100 $m^2/g$, 150 $m^2/g$, 250 $m^2/g$, or 300 $m^2/g$ to 500 $m^2/g$, 525 $m^2/g$, 550 $m^2/g$, or 600 $m^2/g$. In some embodiments, the ZSM-11 zeolite can have a micropore surface area of from 100 $m^2/g$ to 600 $m^2/g$, 250 $m^2/g$ to 500 $m^2/g$, or 300 $m^2/g$ to 500 $m^2/g$.

The ZSM-11 zeolite can have an external surface area of from 20 $m^2/g$, 40 $m^2/g$, 50 $m^2/g$, or 100 $m^2/g$ to 150 $m^2/g$, 200 $m^2/g$, 225 $m^2/g$, or 250 $m^2/g$. In some embodiments, the ZSM-11 zeolite can have an external surface area of from 20 $m^2/g$ to 250 $m^2/g$, 100 $m^2/g$ to 200 $m^2/g$, or 100 $m^2/g$ to 150 $m^2/g$.

In some embodiments, the ZSM-11 zeolite can have a micropore surface area of from 100 $m^2/g$ to 600 $m^2/g$ and an external surface area of from 20 $m^2/g$ to 250 $m^2/g$. In other embodiments, the ZSM-11 zeolite can have a micropore surface area of from 250 $m^2/g$ to 500 $m^2/g$ and an external surface area of from 100 $m^2/g$ to 200 $m^2/g$. In other embodiments, the ZSM-11 zeolite can have a micropore surface area of from 300 $m^2/g$ to 500 $m^2/g$ and an external surface area of from 100 $m^2/g$ to 150 $m^2/g$.

The total surface area and the micropore surface area can be measured via the well-known Brunauer-Emmett-Teller (BET) method. The total surface area and the t-Plot micropore surface area can be measured by nitrogen adsorption/desorption after degassing of the extrudate for 4 hours at 350° C. As noted above, the external surface area can obtained by subtracting the t-plot micropore surface area from the total surface area. More information regarding the method can be found, for example, in "Characterization of Porous Solids and Powders: Surface Area, Pore Size and Density", S. Lowell et al., Springer, 2004.

The ZSM-11 zeolite, when examined with a scanning electron microscope (SEM) or a transmission electron microscope (TEM), can appear as primary crystals and/or as aggregates of primary crystals. Primary crystals and aggregates of primary crystals are described in C. R. Chimie 20 (2017) 1083-1092. In some embodiments, the ZSM-11 zeolite can be in the form of crystals having a crystallite size in a range from 10 nm, 50 nm, 100 nm, or 250 nm to 500 nm, 650 nm, 800 nm, 900 nm, or 1,000 nm, as determined by SEM or TEM. The term "crystallite", as used herein, refers to the primary crystals. In other embodiments the ZSM-11 zeolite can be in the form of crystals having a crystallite size of ≤200 nm, ≤150 nm, ≤100 nm, ≤80 nm, ≤70 nm, ≤60 nm, ≤50 nm, or ≤30 nm. In some embodiments, the ZSM-11 zeolite can include, based on a total number of primary crystals, ≥75%, ≥80%, ≥85%, ≥90%, ≥95%, up to 98% of primary crystals having a size as determined by SEM or TEM analysis of ≤1,000 nm, ≤750 nm, ≤500 nm, ≤400 nm, ≤300 nm, ≤200 nm, ≤150 nm, ≤100 nm, ≤80 nm, ≤70 nm, ≤60 nm, ≤50 nm, ≤50 nm, or ≤30 nm. The ZSM-11 zeolite crystals can form a number of agglomerates with irregular shapes. The ZSM-11 zeolite can be in the form of primary crystals having non-needle and non-fiber morphology and can have a length to diameter ratio of ≤5, ≤4, ≤3, or ≤2. The length to diameter ratio can be determined via SEM or TEM analysis.

Process for Making the ZSM-11 Zeolite

The ZSM-11 zeolite can be made via any suitable process. In some embodiments, ZSM-11 crystals can be synthesized from a reaction mixtures of DI water, tetra-n-butylammonium bromide (TBABr), ULTRASIL® silica, aluminum sulfate solution, 50% sodium hydroxide solution, and ZSM-11 seeds.

Catalyst Composition

In some embodiments, the ZSM-11 zeolite can be used directly as a catalyst, i.e., the ZSM-11 zeolite can be substantially free of any other component other than the ZSM-11 zeolite. In such embodiment, the ZSM-11 zeolite can be a self-supported catalyst composition.

In some embodiments, the ZSM-11 zeolite can be combined with a second zeolite, such as zeolites having a 10- or 12-member ring structure in their crystallites. Non-limiting examples of second zeolites can be or can include, but are not limited to, ZSM-5, ZSM-12, ZSM-22, ZSM-23, ZSM-35, ZSM-48, ZSM-57, ZSM-58, or any mixture thereof. In some embodiments, the second zeolite, if present, can be or can include one or more of the zeolites described in U.S. Pat. No. 3,702,886; RE29,948; 3,832,449; 4,556,477; 4,076,842; 4,016,245); 4,397,827); and 4,417,780.

If one or more second zeolites are included in the catalyst, the catalyst can include 1 wt %, 5 wt %, 10 wt %, 20 wt %, 30 wt %, or 40 wt % to 60 wt %, 70 wt %, 80 wt %, 90 wt %, or 99 wt % of the ZSM-11 zeolite, based on the total weight of the ZSM-11 zeolite and the one or more second zeolites. When the catalyst includes multiple second zeolites, each second zeolite can be present in any amount with respect to one another.

In some embodiments, the ZSM-11 zeolite can be combined with the second zeolite, e.g., the ZSM-5 zeolite, via simple mixing. In other embodiments, the ZSM-11 zeolite and the second zeolite, e.g., the ZSM-5 zeolite, can be a ZSM-11/second zeolite intergrowth zeolite, e.g., a ZSM-5/ZSM-11 intergrowth zeolite. Some ZSM-5/ZSM-11 intergrowth zeolites are disclosed in G. A. Jablonski, L. B. Sand, and J. A. Gard, Zeolites, Vol. 6, Issue 5, pgs. 396-402 (1986) and G. R. Millward, S. Ramdas, J. M. Thomas, and M. T. Barlow, J. Chem. Soc., Faraday Trans. 2, 1983, 79, 1075-1082. In some embodiments, the ZSM-5/ZSM-11 intergrowth zeolite can include 50 wt %, 60 wt %, 70 wt %, or 80 wt % to 90 wt %, 95 wt %, 98 wt %, or 99 wt % of the ZSM-11 zeolite, based on a combined weight of the ZSM-11 zeolite and the ZSM-5 zeolite.

In some embodiments, the ZSM-11 zeolite can be compounded with one or more other components such as binders or matrix materials that serve as a support and/or provide additional hardness to the finished catalyst. The binders or matrix materials can serve as a diluent to control the amount of conversion in a given process so that products can be obtained in an economic and orderly manner without employing other means for controlling the rate of reaction.

Binders can be or can include, but are not limited to, alumina, silica, titania, zirconia, zirconium silicate, kaolin, one or more chromium oxides, other refractory oxides and refractory mixed oxides, and mixtures and combinations thereof. In some embodiments, the ZSM-11 zeolite can be composited with a porous binary matrix material such as silica-alumina, silica-magnesia, silica-zirconia, silica-thoria, silica-beryllia, silica-titania as well as ternary matrix material such as silica-alumina-thoria, silica-alumina-zirconia silica-alumina-magnesia and silica-magnesia-zirconia. Suitable matrix materials can be or can include, but are not limited to, naturally occurring clays, e.g., montmorillonite, bentonite, subbentonite and kaolin such as the kaolins commonly known as Dixie, McNamee, Georgia, and Florida clays or others in which the main mineral constituent is halloysite, kaolinite, nacrite or anauxite, to improve the crush strength of the catalyst under commercial operating conditions. Such clays can be used in the raw state as originally mined or after being subjected to calcination, acid treatment, and/or chemical modification.

In some embodiments, the ZSM-11 zeolite can be used in the form of an extrudate with a binder. The extrudate can be formed by extruding a mixture of the catalyst that is or includes the ZSM-11 zeolite and the binder. In some embodiments, the extrudate can be dried and calcined. It should be understood that the catalyst that includes the ZSM-11 zeolite can take any shape: cylinder, solid sphere, trilobe, quadrulobe, eggshell sphere, and the like. In some embodiments, the catalyst that includes the ZSM-11 zeolite, e.g., the ZSM-11 zeolite alone, an extrudate that includes the ZSM-11 zeolite, and/or the ZSM-11 zeolite and one or more second zeolites, can be ground into a powder and used as such.

In some embodiments, the binder in the catalyst that includes the ZSM-11 zeolite can be relatively high surface area binders, such as alumina and/or silica having a specific area of ≥200 m$^2$/g or ≥250 m$^2$/g. In other embodiments, the binder in the catalyst that includes the ZSM-11 zeolite can be relatively low surface area binders, such as alumina and/or silica having a specific area of ≤150 m$^2$/g.

In making the catalyst, the as-synthesized or calcined ZSM-11 zeolite can be mixed with other materials such as the binder, a second zeolite, and/and other components such as water. The mixture can be formed into the desired shape by, e.g., extrusion, molding, and the like. The thus formed catalyst can be optionally dried and/or calcined in nitrogen and/or air to produce the catalyst. It should be understood that the term "extrudate" includes catalysts made via extrusion, molding, or any other process in which the ZSM-11 zeolite is combined with one or more other components such as a binder.

In some embodiments, the catalyst can be an extrudate that can include the ZSM-11 zeolite and a binder, e.g., alumina and/or silica. Such extrudate can include 1 wt % to 100 wt % of the ZSM-11 zeolite and 0 wt % to 99 wt % of the binder. For example, the extrudate can include 1 wt %, 20 wt %, 40 wt %, or 50 wt % to 70 wt %, 80 wt %, 90 wt %, 95 wt %, or 99 wt % of the ZSM-11 zeolite and 1 wt %, 5 wt %, 10 wt %, 20 wt %, or 30 wt % to 50 wt %, 60 wt %, 80 wt %, or 99 wt % of the binder, based on the combined weight of the ZSM-11 zeolite and the binder.

An extrudate that includes the ZSM-11 zeolite and a binder, e.g., alumina and/or silica, can have a total surface area of from 80 m²/g, 100 m²/g, 125 m²/g, 150 m²/g, 175 m²/g, 200 m²/g, or 250 m²/g to 600 m²/g, 650 m²/g, 700 m²/g, 800 m²/g, 900 m²/g, or 1,000 m²/g. In some embodiments, the extrudate can have a total surface area of from 80 m²/g to 1,000 m²/g, 200 m²/g to 700 m²/g, or 300 m²/g to 600 m²/g.

An extrudate that includes the ZSM-11 zeolite and a binder, e.g., alumina and/or silica, can have a micropore surface area of from 50 m²/g, 75 m²/g, 100 m²/g, 110 m²/g, 125 m²/g, 140 m²/g, or 150 m²/g to 300 m²/g, 325 m²/g, 350 m²/g, 400 m²/g, 450 m²/g, 500 m²/g, 550 m²/g, or 600 m²/g. In some embodiments, the extrudate can have a micropore surface area of from 50 m²/g to 600 m²/g, 100 m²/g to 450 m²/g, or 150 m²/g to 300 m²/g.

An extrudate that includes the ZSM-11 zeolite and a binder, e.g., alumina and/or silica, can have an external surface area of from 30 m²/g, 40 m²/g, 50 m²/g, 60 m²/g, 75 m²/g, 90 m²/g, or 100 m²/g to 300 m²/g, 310 m²/g, 320 m²/g, 330 m²/g, 340 m²/g, 350 m²/g, 360 m²/g, 375 m²/g, or 400 m²/g. In some embodiments, the extrudate can have an external surface area of from 30 m²/g to 400 m²/g, 50 m²/g to 400 m²/g, or 100 m²/g to 300 m²/g.

In some embodiments, an extrudate that includes the ZSM-11 zeolite and a binder, e.g., alumina and/or silica, can have a micropore surface area of from 50 m²/g to 600 m²/g and an external surface area of from 30 m²/g to 400 m²/g. In other embodiments, an extrudate that includes the ZSM-11 zeolite and a binder, e.g., alumina and/or silica, can have a micropore surface area of from 100 m²/g to 450 m²/g and an external surface area of from 50 m²،/g to 400 m²/g. In other embodiments, an extrudate that includes the ZSM-11 zeolite and a binder, e.g., alumina and/or silica, can have a micropore surface area of from 150 m²/g to 300 m²/g and an external surface area of from 100 m²/g to 300 m²/g.

In some embodiments, the ZSM-11 zeolite can have an alpha value of 1 to 3,000, a silica to alumina molar ratio of from 15 to 200, a micropore surface area of from 100 m²/g to 600 m²/g and an external surface area of from 20 m²/g to 250 m²/g, and an extrudate that includes the ZSM-11 zeolite and a binder, e.g., alumina and/or silica, can have a micropore surface area of from 50 m²/g to 600 m²/g and an external surface area of from 30 m²/g to 400 m²/g. In other embodiments, the ZSM-11 zeolite can have an alpha value of 20 to 2,000, a silica to alumina molar ratio of from 20 to 100, a micropore surface area of from 250 m²/g to 500 m²/g and an external surface area of from 100 m²/g to 200 m²/g, and an extrudate that includes the ZSM-11 zeolite and a binder, e.g., alumina and/or silica, can have a micropore surface area of from 100 m²/g to 450 m²/g and an external surface area of from 50 m²/g to 400 m²/g. In other embodiments, the ZSM-11 zeolite can have an alpha value of 20 to 1000, a silica to alumina molar ratio of from 20 to 80, a micropore surface area of from 300 m²/g to 500 m²/g and an external surface area of from 100 m²/g to 150 m²/g, and an extrudate that includes the ZSM-11 zeolite and a binder, e.g., alumina and/or silica, can have a micropore surface area of from 150 m²/g to 300 m²/g and an external surface area of from 100 m²/g to 300 m²/g.

Procedures for preparing silica bound zeolites are described in U.S. Pat. Nos. 4,582,815; 5,053,374; and 5,182,242. A particular procedure for binding ZSM-11 with a silica binder involves an extrusion process. In some embodiments, preparing a silica bound ZSM-11 zeolite can include mixing and extruding a mixture that can include water, ZSM-11 zeolite, colloidal silica, and sodium ions under conditions sufficient to form an uncalcined extrudate having an intermediate green strength sufficient to resist attrition during an ion exchange step. The uncalcined extrudate can be contacted with an aqueous solution that can include ammonium cations under conditions sufficient to exchange cations in the ZSM-11 zeolite with ammonium cations to produce an ammonium exchanged extrudate. The ammonium exchanged extrudate can be calcined under conditions sufficient to generate a hydrogen form of the ZSM-11 zeolite and increase the crush strength of said extrudate.

Another process of silica binding can use a suitable silicone resin, e.g., a high molecular weight, hydroxy functional silicone, such as Dow Corning Q6-2230 silicone resin in a method disclosed in U.S. Pat. No. 4,631,267. Other silicone resins can include those described in U.S. Pat. No. 3,090,691. When a silicone resin is used, a suitable polar, water soluble carrier, such as methanol, ethanol, isopropyl alcohol, N-methyl pyrrolidone or a dibasic ester can also be used along with water as needed. Dibasic esters that may be useful in this invention include dimethyl glutarate, dimethyl succinate, dimethyl adipate, and mixtures thereof.

In some embodiments, extrusion aids can also be used in the preparation of the catalyst. Methyl cellulose is a suitable extrusion aid, and one particular methyl cellulose that can be used can be or can include a hydroxypropyl methyl cellulose, such as K75M METHOCEL®, available from Dow Chemical Co. Methyl cellulose may also be used alone or in combination with other binder or matrix material as a burn-out material to increase the porosity of the catalyst.

In some embodiments, the ZSM-11 zeolite can be at least partially dehydrated prior to contact with the gaseous hydrocarbon feed. The ZSM-11 zeolite can be at least partially dehydrated by heating the ZSM-11 zeolite or the catalyst that includes the ZSM-11 zeolite such as the extrudate to a temperature of 100° C., 150° C., or 200° C. to 300° C., 400° C., or 500° C., e.g., 200° C. to 370° C. The ZSM-11 zeolite or catalyst that includes the ZSM-11 zeolite can be heated in a suitable atmosphere such as air, nitrogen, etc. The ZSM-11 zeolite or catalyst that includes the ZSM-11 zeolite can be heated at atmospheric, subatmospheric, or superatmospheric pressure. The ZSM-11 zeolite or catalyst that includes the ZSM-11 zeolite can be heated for 30 minutes, 1 hour, 6 hours, 10 hours, 12 hours, or 18 hours to 20 hours, 24 hours, 30 hours, 36 hours, 42 hours, or 48 hours. Dehydration can also be performed at room temperature merely by placing the ZSM-11 zeolite or the catalyst that includes the ZSM-11 zeolite in a vacuum, but a longer time can be required to obtain a preferred amount of dehydration.

Isomerization Process

In some embodiments, a gaseous hydrocarbon feed that includes C8 aromatic hydrocarbons, e.g., meta-xylene and/or ortho-xylene, can be contacted with the catalyst that can be or can include the ZSM-11 zeolite in a conversion zone under conversion zone conditions to effect isomerization of at least a portion of the C8 aromatic hydrocarbons to produce a conversion product rich in para-xylene. The isomerization can be carried out under conditions such that the C8 aromatic hydrocarbons are substantially in the vapor phase in the presence of the catalyst that includes the ZSM-11 zeolite.

The gaseous hydrocarbon feed and the catalyst can be contacted with one another at a temperature of 200° C., 250° C., 300° C., or 350° C. to 400°, 450° C., 500° C., 550° C., or 600° C. In some embodiments, the gaseous hydrocarbon feed and the catalyst can be contacted with one another at a temperature of 200° C. to 600° C., 300° C. to 500° C., or 350° C. to 450° C. The gaseous hydrocarbon feed can be contacted with the catalyst at a WHSV of 0.1 hr$^{-1}$, 0.5 hr$^{-1}$, 1 hr$^{-1}$, 5 hr$^{-1}$, or 10 hr$^{-1}$ to 12 hr$^{-1}$, 18 hr$^{-1}$, 24 hr$^{-1}$, 36 hr$^{-1}$, 48 hr$^{-1}$, or 60 hr$^{-1}$. In some embodiments, the gaseous hydrocarbon feed and can be contacted with the catalyst at a WHSV of 0.1 hr$^{-1}$ to 60 hr$^{-1}$, 5 hr$^{-1}$ to 60 hr$^{-1}$, or 10 hr$^{-1}$ to 48 hr$^{-1}$. In some embodiments, the gaseous hydrocarbon feed and the catalyst can be contacted with one another in the presence of molecular hydrogen. The molecular hydrogen can be introduced as a component of the gaseous hydrocarbon feed, introduced into the conversion zone, or a combination thereof. The molar ratio of molecular hydrogen to hydrocarbons in the gaseous hydrocarbon feed within the conversion zone can be from 0.01, 0.05, 0.1, 0.5, 0.7, or 0.8 to 1, 1.3, 1.5, 1.7, or 2.

In some embodiments, the gaseous hydrocarbon feed that includes C8 aromatic hydrocarbons, e.g., ethylbenzene and meta-xylene and/or ortho-xylene, can be contacted with a first catalyst, e.g., a ZSM-5 zeolite and/or a ZSM-11 zeolite, in a first conversion zone under first conversion zone conditions to effect conversion of at least a portion of the ethylbenzene into benzene and ethane to produce an effluent lean in ethylbenzene. The conversion of the ethylbenzene can be carried out under conditions such that the C8 aromatic hydrocarbons are substantially in the vapor phase. The gaseous hydrocarbon feed and the first catalyst can be contacted with one another at a temperature of 200° C., 250° C., 300° C., or 350° C. to 400°, 450° C., 500° C., 550° C., or 600° C. In some embodiments, the gaseous hydrocarbon feed and the first catalyst can be contacted with one another at a temperature of 200° C. to 600° C., 300° C. to 500° C., or 350° C. to 450° C. The gaseous hydrocarbon feed can be contacted with the first catalyst at a WHSV of 0.1 hr$^{-1}$, 0.5 hr$^{-1}$, 1 hr$^{-1}$, 5 hr$^{-1}$, or 10 hr$^{-1}$ to 12 hr$^{-1}$, 18 hr$^{-1}$, 24 hr$^{-1}$, 36 hr$^{-1}$, 48 hr$^{-1}$, or 60 hr$^{-1}$. In some embodiments, the gaseous hydrocarbon feed and can be contacted with the first catalyst at a WHSV of 0.1 hr$^{-1}$ to 60 hr$^{-1}$, 5 hr$^{-1}$ to 60 hr$^{-1}$, or 10 hr$^{-1}$ to 48 hr$^{-1}$. In some embodiments, the gaseous hydrocarbon feed and the first catalyst can be contacted with one another in the presence of molecular hydrogen. The molecular hydrogen can be introduced as a component of the gaseous hydrocarbon feed, introduced into the first conversion zone, or a combination thereof. The molar ratio of molecular hydrogen to hydrocarbons in the gaseous hydrocarbon feed within the first conversion zone can be from 0.01, 0.05, 0.1, 0.5, 0.7, or 0.8 to 1, 1.3, 1.5, 1.7, or 2.

The effluent lean in ethylbenzene can be contacted with a second catalyst that can be or can include the ZSM-11 zeolite in a second conversion zone under second conversion zone conditions to effect isomerization of at least a portion of any meta-xylene, at least a portion of any ortho-xylene, or both to produce a conversion product rich in para-xylene. The isomerization can be carried out under conditions where the C8 aromatic hydrocarbons are substantially in the vapor phase in the presence of the second catalyst that includes the ZSM-11 zeolite. The effluent lean in ethylbenzene and the second catalyst can be contacted with one another at a temperature of 200° C., 250° C., 300° C., or 350° C. to 400°, 450° C., 500° C., 550° C., or 600° C. In some embodiments, the effluent lean in ethylbenzene and the second catalyst can be contacted with one another at a temperature of from 200° C. to 600° C., 300° C. to 500° C., or 350° C. to 450° C. The effluent lean in ethylbenzene can be contacted with the second catalyst at a WHSV of 0.1 hr$^{-1}$, 0.5 hr$^{-1}$, 1 hr$^{-1}$, 5 hr$^{-1}$, or 10 hr$^{-1}$ to 12 hr$^{-1}$, 18 hr$^{-1}$, 24 hr$^{-1}$, 36 hr$^{-1}$, 48 hr$^{-1}$, or 60 hr$^{-1}$. In some embodiments, the effluent lean in ethylbenzene and can be contacted with the second catalyst at a WHSV of 0.1 hr$^{-1}$ to 60 hr$^{-1}$, 5 hr$^{-1}$ to 60 hr$^{-1}$, or 10 hr$^{-1}$ to 48 hr$^{-1}$. In some embodiments, the effluent lean in ethylbenzene and the second catalyst can be contacted with one another in the presence of molecular hydrogen. The molecular hydrogen can be introduced as a component of the gaseous hydrocarbon feed, introduced into the second conversion zone, or a combination thereof. The molar ratio of molecular hydrogen to hydrocarbons in the effluent lean in ethylbenzene within the second conversion zone can be from 0.01, 0.05, 0.1, 0.5, 0.7, or 0.8 to 1, 1.3, 1.5, 1.7, or 2.

In other embodiments, the gaseous hydrocarbon feed that includes C8 aromatic hydrocarbons, e.g., ethylbenzene and meta-xylene and/or ortho-xylene, can be contacted with a first catalyst, e.g., a ZSM-5 zeolite and/or a ZSM-11 zeolite, in a first conversion zone under first conversion zone conditions to effect isomerization of at least a portion of any meta-xylene, at least a portion of any ortho-xylene, or both to produce an effluent rich in para-xylene. The isomerization can be carried out under conditions where the C8 aromatic hydrocarbons are substantially in the vapor phase in the presence of the first catalyst. The gaseous hydrocarbon feed and the first catalyst can be contacted with one another at a temperature of from 200° C., 250° C., 300° C., or 350° C. to 400°, 450° C., 500° C., 550° C., or 600° C. In some embodiments, the gaseous hydrocarbon feed and the first catalyst can be contacted with one another at a temperature of from 200° C. to 600° C., 300° C. to 500° C., or 350° C. to 450° C. The gaseous hydrocarbon feed can be contacted with the first catalyst at a WHSV of 0.1 hr$^{-1}$, 0.5 hr$^{-1}$, 1 hr$^{-1}$, 5 hr$^{-1}$, or 10 hr$^{-1}$ to 12 hr$^{-1}$, 18 hr$^{-1}$, 24 hr$^{-1}$, 36 hr$^{-1}$, 48 hr$^{-1}$, or 60 hr$^{-1}$. In some embodiments, the gaseous hydrocarbon feed can be contacted with the first catalyst at a WHSV of 0.1 hr$^{-1}$ to 60 hr$^{-1}$, 5 hr$^{-1}$ to 60 hr$^{-1}$, or 10 hr$^{-1}$ to 48 hr$^{-1}$. In some embodiments, the gaseous hydrocarbon feed and the first catalyst can be contacted with one another in the presence of molecular hydrogen. The molecular hydrogen can be introduced as a component of the gaseous hydrocarbon feed, introduced into the first conversion zone, or a combination thereof. The molar ratio of molecular hydrogen to hydrocarbons in the hydrocarbon-containing feed within the second conversion zone can be from 0.01, 0.05, 0.1, 0.5, 0.7, or 0.8 to 1, 1.3, 1.5, 1.7, or 2.

The effluent rich in para-xylene ethylbenzene can be contacted with a second catalyst that can be or can include a second catalyst, e.g., a ZSM-5 zeolite and/or a ZSM-11 zeolite in a second conversion zone under second conversion zone conditions to effect conversion of at least a portion of the ethylbenzene into benzene and ethane to produce a conversion product lean in ethylbenzene. The conversion of the ethylbenzene can be carried out under conditions such that the C8 aromatic hydrocarbons are substantially in the vapor phase. The effluent and the second catalyst can be contacted with one another at a temperature of from 200° C., 250° C., 300° C., or 350° C. to 400°, 450° C., 500° C., 550° C., or 600° C. In some embodiments, the effluent and the second catalyst can be contacted with one another at a temperature of from 200° C. to 600° C., 300° C. to 500° C., or 350° C. to 450° C. The effluent can be contacted with the second catalyst at a WHSV of 0.1 hr$^{-1}$, 0.5 hr$^{-1}$, 1 hr$^{-1}$, 5 hr$^{-1}$, or 10 hr$^{-1}$ to 12 hr$^{-1}$, 18 hr$^{-1}$, 24 hr$^{-1}$, 36 hr$^{-1}$, 48 hr$^{-1}$, or 60 hr$^{-1}$. In some embodiments, the effluent can be contacted with the second catalyst at a WHSV of 0.1 hr$^{-1}$ to 60 hr$^{-1}$, 5 hr$^{-1}$ to 60 hr$^{-1}$, or 10 hr$^{-1}$ to 48 hr$^{-1}$. In some embodiments, the effluent and the second catalyst can be contacted with one another in the presence of molecular hydrogen. The molecular hydrogen can be introduced as a component of the hydrocarbon-containing feed, introduced into the second conversion zone, or a combination thereof.

The molar ratio of molecular hydrogen to hydrocarbons in the effluent within the second conversion zone can be from 0.01, 0.05, 0.1, 0.5, 0.7, or 0.8 to 1, 1.3, 1.5, 1.7, or 2.

In some embodiments, the first catalyst, the second catalyst, or the first catalyst and the second catalyst can be or can include a selectivated first catalyst and/or a selectivated second catalyst. Selectivated catalysts include a layer of a material deposited on the surface of the catalyst that can impact the diffusivity of different molecules into the zeolite. In some embodiments, the first catalyst and/or the second catalyst can be subjected to a silica selectivation treatment process and/or a coke selectivation treatment process. The first catalyst and/or the second catalyst can be subjected to one or more treatments with an organosilicon compound in a liquid carrier to produce a treated catalyst, each treatment followed by calcination of the treated catalyst in an oxygen-containing atmosphere, e.g., air. In some embodiments, the first catalyst and/or the second catalyst can be subjected to 1, 2, 3, 4, or more selectivation treatments to produce the selectivated catalyst. In some embodiments, if the first catalyst and/or the second catalyst includes a binder, it can be preferable to use a non-acidic binder, such as silica. Suitable selectivation treatments can include those disclosed in U.S. Pat. Nos. 4,117,026; 5,476,823; and 7,271,118.

The organosilicon compound can be or can include, but is not limited to, a silicone, a siloxane, a silane, or mixture thereof. The organosilicon compound can have at least 2 silicon atoms per molecule. The organosilicon compound can be a solid in pure form, provided that it is soluble or otherwise convertible into a liquid form upon combination with the liquid carrier. The molecular weight of the silicone, siloxane, or silane compound(s) employed as a preselectivating agent can be from 80 to 20,000, e.g., 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane, or silane compound(s) need not be linear, but can be cyclic, for example, hexamethyl cyclotrisiloxane, octamethyl cyclotetrasiloxane, hexaphenyl cyclotrisiloxane and octaphenyl cyclotetra-siloxane. Mixtures of these compounds may also be used as preselectivating agents, as can silicones with other functional groups.

The liquid carrier for the organosilicon compound can be or can include, but is not limited to, one or more organic compounds, such as a linear, branched or cyclic hydrocarbon having five or more, especially 7 or more, carbon atoms per molecule, e.g., an alkane, such as heptane, octane, nonane, or undecane. The boiling point of the organic compound, e.g., alkane, can be greater than 70° C. Mixtures of low volatility organic compounds, such as hydrocracker recycle oil, can be employed as carriers. Particularly preferred organic carriers are decane and dodecane.

Following each impregnation with the organosilicon compound, the catalyst can be calcined at a rate of from 0.2° C./minute to 5° C./minute to a temperature of greater than 200° C., but below the temperature at which the crystallinity of the zeolite is adversely affected. This calcination temperature will generally be below 600° C. and preferably is within the approximate range of 350° C. to 550° C. The duration of calcination at the calcination temperature can be from 1 hour to 24 hours, e.g., from 2 hours to 6 hours.

In addition to, or in place of, silica selectivation, the first catalyst and/or the second catalyst can be subjected to coke selectivation treatment process. Coke selectivation typically involves contacting the catalyst with a thermally decomposable organic compound at an elevated temperature in excess of the decomposition temperature of the decomposable organic compound but below the temperature at which the crystallinity of the zeolite is adversely affected. This contact temperature can be, for example, less than 650° C. Decomposable organic materials that can be used in the coke selectivation process, encompass a wide variety of compounds including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen cofeed can be used to deter the excessive build-up of coke. Further details regarding coke selectivation techniques are provided in the U.S. Pat. No. 4,117,026. By using a combination of silica selectivation followed by coke selectivation, the number of organosilicon impregnation treatments required to achieve a particular xylene diffusivity can be reduced.

As discussed above, an advantage of the process for converting the gaseous C8 aromatic hydrocarbons using the catalyst that includes the ZSM-11 zeolite disclosed herein can be a high para-xylene selectivity in the conversion product and in some embodiments at high WHSV such as >10 $hr^{-1}$, ≥15 $hr^{-1}$, ≥20 $hr^{-1}$, ≥24 $hr^{-1}$, ≥28 $hr^{-1}$, ≥36 $hr^{-1}$, ≥40 $hr^{-1}$, ≥44 $hr^{-1}$, or ≥48 $hr^{-1}$. Thus, in some embodiments, the process for converting the gaseous C8 aromatic hydrocarbons, as disclosed herein, can exhibit a para-xylene selectivity of ≥20%, ≥21%, ≥22%, or ≥23%, at WHSV of 12 $hr^{-1}$ when the C8 aromatic hydrocarbon feed includes para-xylene at a concentration of ≤15 wt %, ≤10 wt %, ≤8 wt %, ≤6 wt %, ≤5 wt %, ≤3 wt %, or ≤2 wt %, based on the total weight of xylenes in the C8 aromatic hydrocarbon feed. In other embodiments, the process for converting the gaseous C8 aromatic hydrocarbons can exhibit a para-xylene selectivity of ≥20%, or ≥21%, or ≥22%, or ≥23% at WHSV of 24 $hr^{-1}$ when the C8 aromatic hydrocarbon feed includes para-xylene at a concentration of ≤15 wt %, ≤10 wt %, ≤8 wt %, ≤6 wt %, ≤5 wt %, ≤3 wt %, or ≤2 wt %, based on the total weight of xylenes in the C8 aromatic hydrocarbon feed. In other embodiments, the process for converting the gaseous C8 aromatic hydrocarbons can exhibit a para-xylene selectivity of ≥20%, or ≥21%, or ≥22%, or ≥23%, at WHSV of 36 $hr^{-1}$ when the C8 aromatic hydrocarbon feed includes para-xylene at a concentration of ≤15 wt %, ≤10 wt %, ≤8 wt %, ≤6 wt %, ≤5 wt %, ≤3 wt %, or ≤2 wt %, based on the total weight of xylenes in the C8 aromatic hydrocarbon feed. In still other embodiments, the process for converting the gaseous C8 aromatic hydrocarbons can exhibit a para-xylene selectivity of ≥18%, or ≥19%, or ≥20%, at WHSV of 48 $hr^{-1}$ when the C8 aromatic hydrocarbon feed includes para-xylene at a concentration of ≤15 wt %, ≤10 wt %, ≤8 wt %, ≤6 wt %, ≤5 wt %, ≤3 wt %, or ≤2 wt %, based on the total weight of xylenes in the C8 aromatic hydrocarbon feed. Such high para-xylene selectivity at such a high WHSV is not achievable in a comparative process using a ZSM-S-based catalyst composition and is particularly advantageous. The fact that the catalyst that includes the ZSM-11 zeolite as disclosed herein can achieve such high para-xylene selectivity at such a high WHSV was surprising and unexpected.

As discussed above, another advantage of the process for converting the gaseous C8 aromatic hydrocarbons using catalyst that includes the ZSM-11 zeolite disclosed herein can be a reduction in xylenes loss in the conversion product. In one embodiment, the ZSM-11 zeolite can have an alpha value of 1 to 3,000, a silica to alumina molar ratio of from 15 to 200, a micropore surface area of from 50 m$^2$/g to 600 m$^2$/g, and an external surface area of from 20 m$^2$/g to 250 m$^2$/g, and the catalyst that includes the ZSM-11 zeolite can be an extrudate that includes the ZSM-11 zeolite and a binder. The extrudate can have a micropore surface area of from 50 m$^2$/g to 600 m$^2$/g and an external surface area of from 30 m$^2$/g to 400 m$^2$/g. In such embodiment, the gaseous hydrocarbon feed can contact the catalyst at a temperature of from 200° C. to 600° C., e.g., 300° C. to 400° C., at a weight hour space velocity of from 12 hr$^{-1}$ to 48 hr$^{-1}$, and exhibit a xylenes loss that can be ≥20%, ≥23%, ≥25%, ≥27%, or ≥30% less as compared to a comparative process operated at the same WHSV and temperature and under a comparable ethylbenzene conversion that uses an extruded catalyst that includes a ZSM-5 zeolite having an alpha value of 1 to 3,000, a silica to alumina molar ratio of from 15 to 200, a micropore surface area of from 50 m$^2$/g to 600 m$^2$/g, and an external surface area of from 20 m$^2$/g to 250 m$^2$/g, where the extrudate has a micropore surface area of from 50 m$^2$/g to 600 m$^2$/g and an external surface area of from 30 m$^2$/g to 400 m$^2$/g.

As discussed above, another advantage of the process for converting the gaseous C8 aromatic hydrocarbons using the catalyst that includes the ZSM-11 zeolite disclosed herein can be a reduced trimethylbenzenes yield in the conversion product. In one embodiment, the ZSM-11 zeolite can have an alpha value of 1 to 3,000, a silica to alumina molar ratio of from 15 to 200, a micropore surface area of from 50 m$^2$/g to 600 m$^2$/g, and an external surface area of from 30 m$^2$/g to 400 m$^2$/g, and the catalyst that includes the ZSM-11 zeolite can be an extrudate that includes the ZSM-11 zeolite and a binder. The extrudate can have a micropore surface area of from 50 m$^2$/g to 600 m$^2$/g and an external surface area of from 30 m$^2$/g to 400 m$^2$/g. In such embodiment, the gaseous hydrocarbon feed can contact the catalyst at a temperature of from 200° C. to 600° C., e.g., 300° C. to 400° C., at a weight hour space velocity of from 12 hr$^{-1}$ to 48 hr$^{-1}$, and exhibit a reduction of ≥25%, ≥30%, ≥35%, ≥37%, or ≥40% in the production of trimethylbenzenes as compared to a comparative process operated at the same WHSV and temperature and under a comparable ethylbenzene conversion that uses an extruded catalyst that includes a ZSM-5 zeolite having an alpha value of 1 to 3000, a silica to alumina molar ratio of from 15 to 200, a micropore surface area of from 50 m$^2$/g to 600 m$^2$/g, and an external surface area of from 30 m$^2$/g to 400 m$^2$/g, where the extrudate has a micropore surface area of from 50 m$^2$/g to 400 m$^2$/g and an external surface area of from 30 m$^2$/g to 400 m$^2$/g.

The conversion processes described herein can be carried out as a batch type, semi-continuous, or continuous operation. After use in a moving or fluidized bed reactor, the catalyst(s) can be regenerated in a regeneration zone in which coke is burned from the catalyst(s) in an oxygen containing atmosphere, e.g., air, at an elevated temperature after which the regenerated catalyst can be recycled to the conversion zone, the first conversion zone, or the second conversion zone, depending on the particular process configuration. In a fixed bed reactor, regeneration can be carried out in a conventional manner by using initially an inert gas containing a small amount of oxygen (0.5 vol % to 10 vol %) to burn coke in a controlled manner.

In some embodiments, the xylene isomerization reaction can be carried out in a fixed bed reactor. In one embodiment, the catalyst that includes the ZSM-11 zeolite can be disposed in a catalyst bed located within the conversion zone and the gaseous hydrocarbon feed can be contacted therewith. In another embodiment, the first catalyst, e.g., a ZSM-5 zeolite and/or a ZSM-11 zeolite can be disposed in a first bed and the second catalyst that includes the ZSM-11 zeolite can be disposed in a second catalyst bed such that the gaseous hydrocarbon feed sequentially contacts the first catalyst and the second catalyst.

In some embodiments, the conversion process can be carried out in two different reactors, even at different process conditions, such as temperatures. For example, the ethylbenzene conversion reaction could be carried out at a higher temperature than the xylene isomerization reaction. Further, when two different reactors are used, benzene, paraxylene, or other aromatics, could be removed between the reactors, thus further reducing the xylenes losses due to transalkylation or other reactions in the xylene isomerization reactor. An additional alternative would be where the ethylbenzene conversion reactor is located outside the xylene recovery and isomerization loop. The gaseous hydrocarbon feed can be cascaded over the first and second catalysts disposed in sequential beds. In cascading, the gaseous hydrocarbon feed can be contacted with the two components of the catalyst system without intervening separation of light gases or materials such as benzene.

The first catalyst that can be effective for ethylbenzene conversion can be upstream with respect to the second catalyst that includes the ZSM-11 zeolite and that can be effective for the conversion of meta-xylene and/or ortho-xylene to para-xylene. The first catalyst and the second catalyst can be employed in amounts relative to one another so that the process can achieve the desired level of ethylbenzene conversion and the desired level of metal-xylene and/or ortho-xylene conversion to para-xylene. In some embodiments, a weight ratio of the first catalyst that is primarily responsible for ethylbenzene conversion to the second catalyst that includes the ZSM-11 zeolite and is primarily responsible for meta-xylene and/or ortho-xylene conversion to para-xylene can be from 1, 1.5, or 2 to 2.5, 3, or 4.

The Gaseous Hydrocarbon Feed

The gaseous hydrocarbon feed that includes the C8 aromatic hydrocarbons can be derived from, e.g., an effluent from a C8 aromatic hydrocarbon distillation column, a para-xylene depleted raffinate stream produced from a para-xylene separation/recovery system that includes an adsorption chromatography system, and/or a para-xylene depleted filtrate stream produced from a para-xylene separation/recovery system that includes a para-xylene crystallizer, or a mixture thereof. In this disclosure, the raffinate stream and the filtrate stream are collectively referred to as a raffinate stream below.

The gaseous hydrocarbon feed that includes C8 aromatics can include para-xylene at various concentrations. In some embodiments, the gaseous hydrocarbon feed can include 0.5 wt %, 1 wt %, 2 wt %, 3 wt %, 4 wt %, 5 wt %, 6 wt %, 7 wt %, 8 wt %, 9 wt %, or 10 wt % to 11 wt %, 12 wt %, 13 wt %, 14 wt %, 15 wt %, 16 wt %, 17 wt %, 18 wt %, 19 wt %, or 20 wt % of para-xylene. Typically the concentration of para-xylene can be lower than the para-xylene concentration in an equilibrium mixture consisting of para-xylene, meta-xylene, and ortho-xylene at the same temperature. In some embodiments, the concentration of para-xylene in the gaseous hydrocarbon feed can be ≤15 wt %, ≤10 wt %, ≤8 wt %, ≤6 wt %, ≤4 wt %, ≤3 wt %, or ≤2 wt %.

The gaseous hydrocarbon feed that includes C8 aromatics can include meta-xylene at various concentrations. In some embodiments, the gaseous hydrocarbon feed can include 20 wt %, 25 wt %, 30 wt %, 35 wt %, 40 wt %, 45 wt %, or 50 wt % to 55 wt %, 60 wt %, 65 wt %, 70 wt %, 75 wt %, or 80 wt % of meta-xylene. In some embodiments, the concentration of meta-xylene can be significantly higher than the meta-xylene concentration in an equilibrium mixture consisting of para-xylene, meta-xylene, and ortho-xylene at the same temperature, especially if the aromatic hydrocarbon feed consists essentially of xylenes only and is substantially free of ethylbenzene.

The gaseous hydrocarbon feed that includes C8 aromatics can include ortho-xylene at various concentrations. In some embodiments, the gaseous hydrocarbon feed can include 10 wt %, 15 wt %, 20 wt %, or 25 wt % to 30 wt %, 35 wt %, 40 wt %, 45 wt %, or 50 wt % of ortho-xylene. In some embodiments, the concentration of ortho-xylene can be significantly higher than the ortho-xylene concentration in an equilibrium mixture consisting of para-xylene, meta-xylene, and ortho-xylene at the same temperature, especially if the aromatic hydrocarbon feed consists essentially of xylenes only and is substantially free of ethylbenzene.

Among all xylenes present in the gaseous hydrocarbon feed, meta-xylene and ortho-xylene can be present at any ratio. Thus, the ratio of meta-xylene to ortho-xylene can be from 0.1, 0.2, 0.3, 0.4, 0.5, 0.6, 0.7, 0.8, 0.9, or 1 to 2, 3, 4, 5, 6, 7, 8, 9, or 10. In some embodiments the gaseous hydrocarbon feed can include xylenes in total at a concentration of 50 wt %, 55 wt %, 60 wt %, 65 wt %, 70 wt %, 75 wt %, or 80 wt % to 85 wt %, 90 wt %, 91 wt %, 92 wt %, 93 wt %, 94 wt %, 95 wt %, 96 wt %, 97 wt %, 98 wt %, 99 wt %, or 100 wt %.

In some embodiments, the gaseous hydrocarbon feed can consist essentially of xylenes and ethylbenzene. The gaseous hydrocarbon feed can include 1 wt %, 2 wt %, 3 wt %, 4 wt %, 5 wt %, 6 wt %, 7 wt %, 8 wt %, 9 wt %, 10 wt %, 12 wt %, 14 wt %, or 15 wt % to 16 wt %, 18 wt %, 20 wt %, 22 wt %, 24 wt %, 25 wt %, 26 wt %, 28 wt %, or 30 wt % of ethylbenzene. In other embodiments, the gaseous hydrocarbon feed can include 2 wt % to 25 wt %, 3 wt % to 20 wt %, or 5 wt % to 15 wt % of ethylbenzene. In other embodiments, the gaseous hydrocarbon feed can be free or substantially free of ethylbenzene. For example, the gaseous hydrocarbon feed can be free of ethylbenzene or can include less than 1 wt %, less than 0.7 wt %, less than 0.5 wt %, less than 0.3 wt %, less than 0.1 wt %, or less than 0.05 wt % of ethylbenzene.

In some embodiments, the gaseous hydrocarbon feed can include C8 aromatic hydrocarbons, i.e., xylenes and ethylbenzene, at an aggregate concentration of 90 wt %, 92 wt %, 94 wt %, or 95 wt % to 96 w %, 98 wt %, 99 wt %, or 100 wt %, based on the total weight of the aromatic hydrocarbon feed. The gaseous hydrocarbon feed can also include C9+ aromatic hydrocarbons. In some embodiments, the gaseous hydrocarbon feed can include 0.1 wt %, 0.5 wt %, 0.7 wt %, 1 wt %, 3 wt %, or 5 wt % to 10 wt %, 15 wt %, 20 wt %, 25 wt %, or 30 wt % of C9+ aromatic hydrocarbons. In some embodiments, the gaseous hydrocarbon feed, depending on its source (e.g., a xylenes distillation column, a p-xylene crystallizer, and/or an adsorption chromatography separation system), can include toluene at various amounts, but typically not greater than 1 wt %, based on the total weight of the gaseous hydrocarbon feed. The gaseous hydrocarbon feed, depending on its source, can also include C7-aromatic hydrocarbons, e.g., toluene and benzene in total, at various amounts.

Recovering a Para-Xylene Product

A high purity para-xylene product can be obtained by separating para-xylene from the conversion product rich in para-xylene that can also include ortho-xylene, meta-xylene, and/or ethylbenzene in a para-xylene separation/recovery system. The para-xylene recovery system can include, e.g., a crystallizer and/or an adsorption chromatography separating system known in the prior art. A para-xylene-depleted product recovered from the para-xylene recovery system (the "filtrate" from a crystallizer upon separation of the para-xylene crystals, or the "raffinate" from the adsorption chromatography separating system, collectively "raffinate") can be rich in meta-xylene and/or ortho-xylene and include para-xylene at a concentration typically below its concentration in an equilibrium mixture consisting of meta-xylene, ortho-xylene, and para-xylene. To increase the yield of para-xylene, the raffinate stream can be fed into an isomerization unit, where the xylenes can undergo isomerization reactions in contacting the catalyst that includes the ZSM-11 zeolite to produce an isomerized effluent rich in para-xylene compared to the raffinate. At least a portion of the isomerized effluent, after optional separation and removal of lighter hydrocarbons that can be produced in the isomerization unit, can be recycled to the para-xylene recovery system, forming a "xylenes loop." The recovery of products from a conversion product that includes para-xylene and one or more of: ethylbenzene, meta-xylene, ortho-xylene, benzene, toluene, trimethylbenzenes can include the processes and systems described in U.S. Pat. Nos. 4,899,011; 5,689,027; 5,977,420; and 8,273,934 and WO Publication No.: 02/088056.

EXAMPLES

The foregoing discussion can be further described with reference to the following non-limiting examples.

Comparative Example 1 (CEx. 1)

Figure 1:
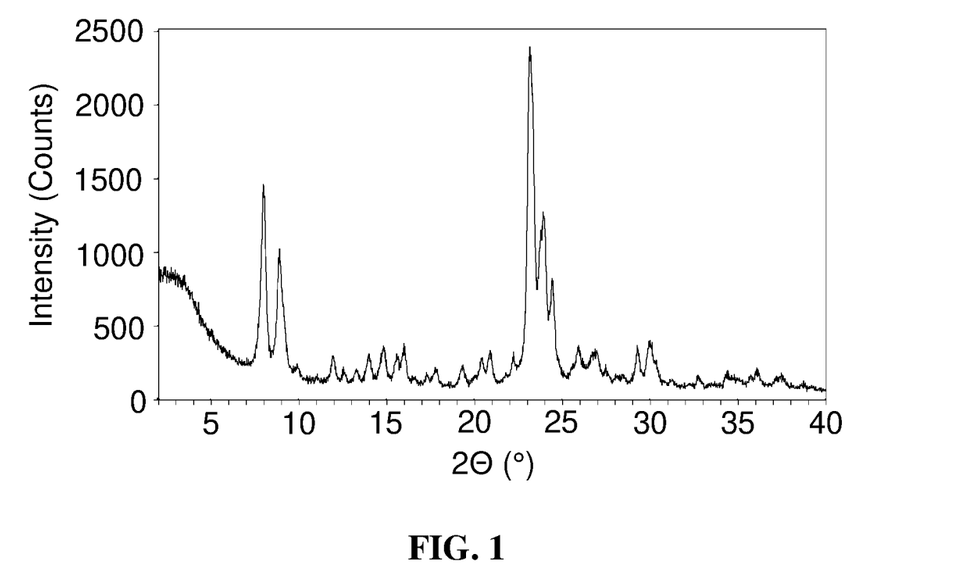
FIG. 1 depicts an XRD pattern of as-synthesized ZSM-5 crystals produced in Comparative Example 1.
Figure 2:
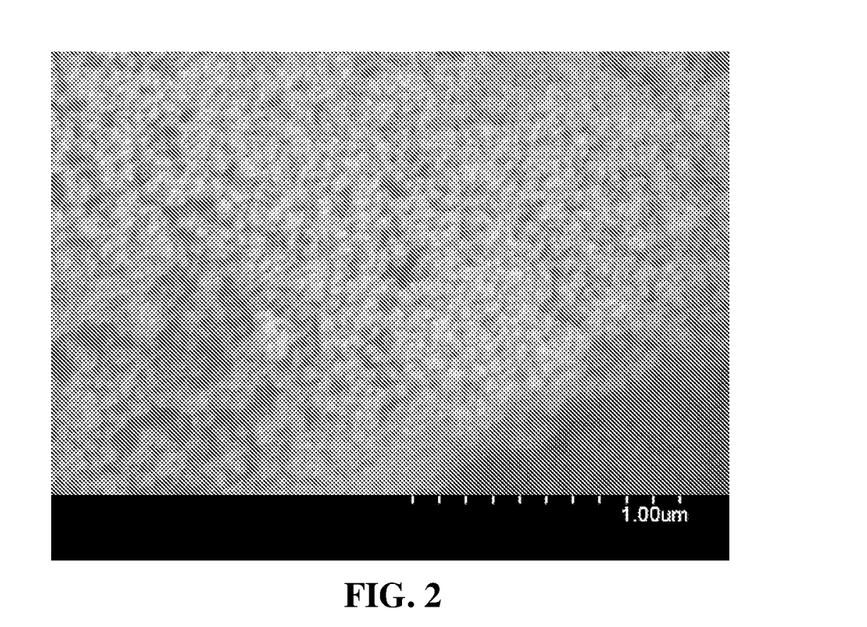
FIG. 2 is an SEM image of the as-synthesized ZSM-5 crystals produced in Comparative Example 1.

ZSM-5 crystals with $Si/Al_2$~26/1 and small crystal size of <0.1 μm were synthesized from a mixture of DI water, tetra-n-butylammonium bromide (TBABr), Silica, Sodium aluminate solution, and caustic solution according to U.S. Pat. No. 4,526,879. The XRD pattern (FIG. 1) of the as-synthesized material showed the typical pure phase of ZSM-5 topology. The SEM of the as-synthesized material showed morphology of agglomerates composed of small crystallites with size of <0.1 micron (FIG. 2). The as-synthesized crystals were pre-calcined in nitrogen at a temperature of 540° C. and then converted into the hydrogen form by three ion exchanges with ammonium nitrate solution at room temperature, followed by drying at a temperature of 120° C. and calcination at a temperature of 540° C. for 6 hours. The resulting ZSM-5 crystals had a $SiO_2/Al_2O_3$ molar ratio of ~26, a total surface area (SA)/(micropore SA+mesopore SA) of 418/(340+78) $m^2/g$, a hexane sorption of ~100 mg/g, and an Alpha of 1300.

Example 1 (Ex. 1)

Figure 3:
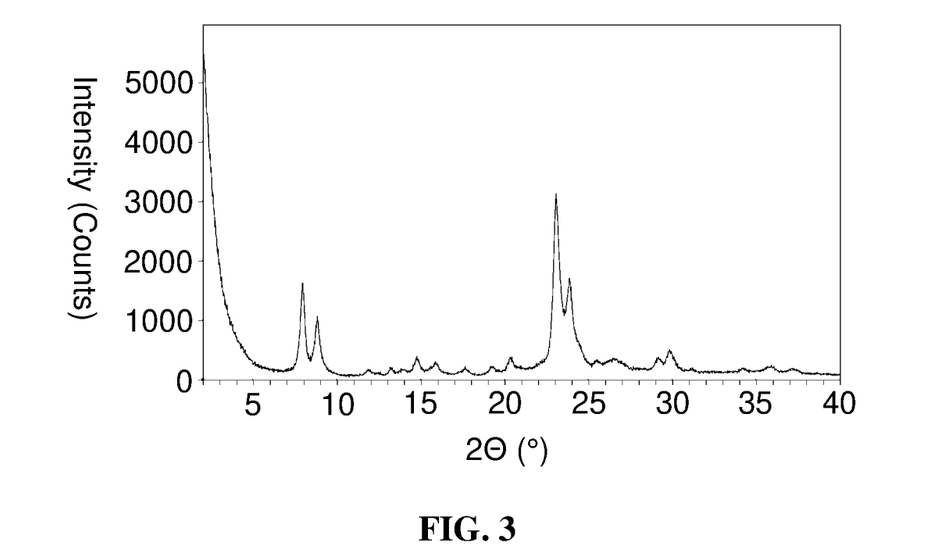
FIG. 3 depicts an XRD pattern of as-synthesized ZSM-11 crystals produced in Example 1.
Figure 4:
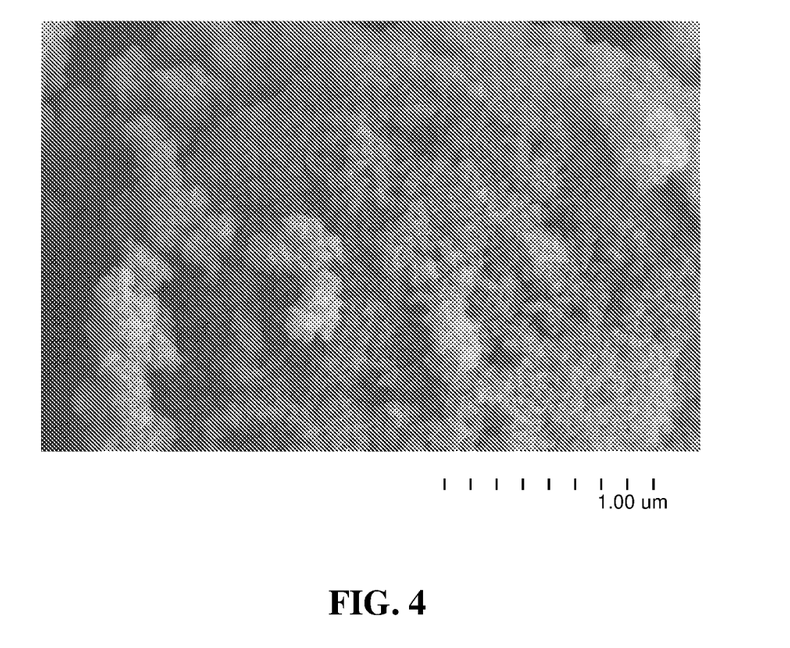
FIG. 4 is an SEM image of the as-synthesized ZSM-11 crystals produced in Example 1.

Small, high activity ZSM-11 crystals were synthesized from a mixture of DI water, TBABr, Ultrasil silica, aluminum sulfate solution, 50% sodium hydroxide solution, and ZSM-11 seeds according to U.S. Pat. No. 3,709,979. The product was filtered, washed with deionized (DI) water, and dried at a temperature of 120° C. The XRD pattern for the resulting crystals (i.e., the as-synthesized material) showed the typical pure phase of ZSM-11 topology (FIG. 3). The SEM of the as-synthesized material showed morphology of agglomerates composed of small crystallites with a size of <0.05 micron (FIG. 4). The as-synthesized crystals were converted into the hydrogen form by three ion exchanges with an ammonium nitrate solution at room temperature, followed by drying at a temperature of 120° C. and calcination at a temperature of 540° C. for 6 hours. The crystals from Example 1 had a $SiO_2/Al_2O_3$ molar ratio of ~25, a total surface area (SA)/(micropore SA+mesopore SA) of 462/(303+158) $m^2/g$, a hexane sorption of ~99 mg/g, and an Alpha of 1300. A much higher external surface area than CEx. 1 was observed primarily due to its smaller crystals size.

Example 2 (Ex. 2)

Figure 5:
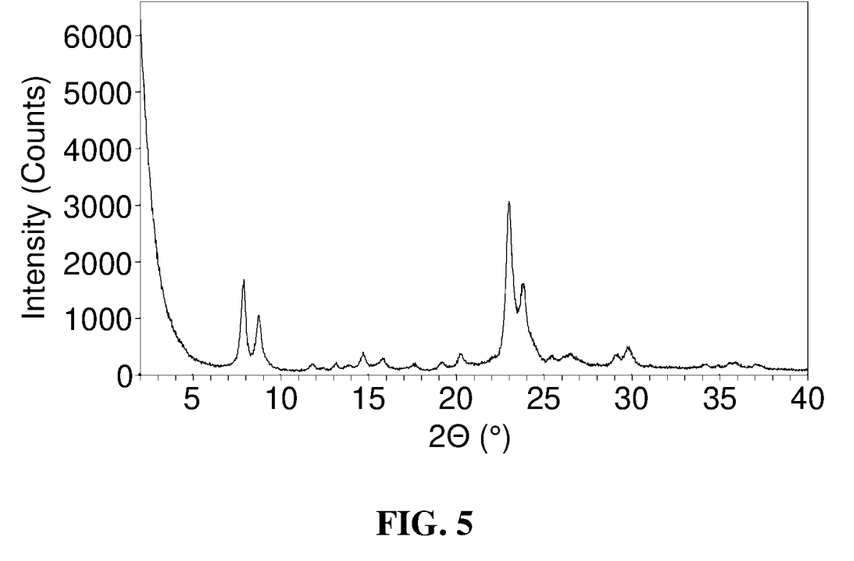
FIG. 5 depicts an XRD pattern of as-synthesized ZSM-11 crystals produced in Example 2.
Figure 6:
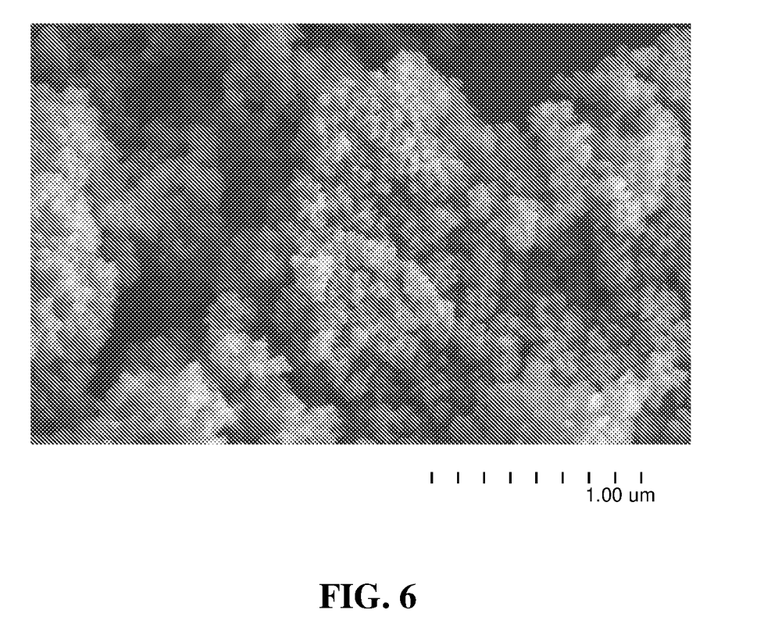
FIG. 6 is an SEM picture of the as-synthesized ZSM-11 crystals produced in Example 2.

Small, medium activity of ZSM-11 crystals were synthesized from a mixture of DI water, TBABr, Ultrasil silica, aluminum sulfate solution, 50% sodium hydroxide solution, and ZSM-11 seeds according to U.S. Pat. No. 3,709,979. The product was filtered, washed with deionized (DI) water, and dried at a temperature of 120° C. The XRD pattern for each of the resulting crystals (i.e., the as-synthesized material) showed the typical pure phase of ZSM-11 topology (FIG. 5). The SEM of the as-synthesized material showed morphology of agglomerates composed of small crystallites with size of <0.05 micron (FIG. 6). The as-synthesized crystals were converted into the hydrogen form by three ion exchanges with ammonium nitrate solution at room temperature, followed by drying at a temperature of 120° C. and calcination at a temperature of 540° C. for 6 hours. The crystals from Example 2 had a $SiO_2/Al_2O_3$ molar ratio of ~50, a total surface area (SA)/(micropore SA+mesopore SA) of 493/(359+134) $m^2/g$, a hexane sorption of 99 mg/g, and an Alpha of ~800. A much higher external surface area than CEx. 1 was observed primarily due to its smaller crystals size.

Comparative Example 2 (CEx. 2)

80 parts (basis: calcined at a temperature of 538° C.) of ZSM-5 crystal from Comparative Example 1 were mixed with 20 parts of ULTRASIL® silica (basis: calcined at a temperature of 538° C.) in a muller. The mixture of ZSM-5, silica, and water was extruded into 1.6 mm (1/16") Q extrudates and dried at a temperature of 121° C. overnight. The dried extrudates were calcined in molecular nitrogen at a temperature of 538° C. for 3 hrs to decompose and remove the organic template. The molecular nitrogen calcined extrudate was humidified with saturated air and exchanged with 1 N ammonium nitrate to remove sodium (spec: <500 ppm Na). After ammonium nitrate exchange, the extrudate was washed with deionized water to remove residual nitrate ions prior to drying. The ammonium exchanged extrudate was dried at a temperature of 121° C. overnight and calcined in air at a temperature of 538° C. for 3 hrs. The H-formed catalyst showed surface area of 372(263+108) $m^2/g$, hexane sorption of ~84.7 mg/g, and an Alpha of ~1300.

Example 3 (Ex. 3)

80 parts (basis: calcined at a temperature of 538° C.) of ZSM-11 crystal from Example 1 were mixed with 20 parts of ULTRASIL® silica (basis: calcined at a temperature of 538° C.) in a muller. The mixture of ZSM-11, silica, and water was extruded into 1.6 mm (1/16") Q extrudates and dried at 121° C. overnight. The dried extrudates were calcined in molecular nitrogen at a temperature of 538° C. for 3 hrs to decompose and remove the organic template. The molecular nitrogen calcined extrudate was humidified with saturated air and exchanged with 1 N ammonium nitrate to remove sodium (spec: <500 ppm Na). After ammonium nitrate exchange, the extrudate was washed with deionized water to remove residual nitrate ions prior to drying. The ammonium exchanged extrudate was dried at a temperature of 121° C. overnight and calcined in air at a temperature of 538° C. for 3 hrs. The H-formed catalyst showed surface area of 430(248+181) $m^2/g$, hexane sorption of ~81 mg/g, and an Alpha of ~1200.

Example 4 (Ex. 4)

80 parts (basis: calcined at a temperature of 538° C.) of ZSM-11 crystal from Example 2 were mixed with 20 parts of VERSAL®-300 alumina (basis: calcined at a temperature of 538° C.) in a muller. The mixture of ZSM-11, alumina, and water was extruded into 1.6 mm (1/16") Q extrudates and then dried at a temperature of 121° C. overnight. The dried extrudates were calcined in molecular nitrogen at a temperature of 538° C. for 3 hrs to decompose and remove the organic template. The molecular nitrogen calcined extrudate was humidified with saturated air and exchanged with 1 N ammonium nitrate to remove sodium (spec: <500 ppm Na). After ammonium nitrate exchange, the extrudates were washed with deionized water to remove residual nitrate ions prior to drying. The ammonium exchanged extrudates were dried at a temperature of 121° C. overnight and calcined in air at a temperature of 538° C. for 3 hrs. H-formed catalyst showed surface area of 452(273+178) $m^2/g$, hexane sorption of ~90.5 mg/g, and Alpha of ~430.

Single Catalyst Bed System Examples

To evaluate the potential performance of the ZSM-11 zeolite as a bottom bed catalyst, the ZSM-11 zeolite was first tested in a single-bed system and compared to the ZSM-5 zeolite in an identical configuration. The gaseous hydrocarbon feed used in the comparative example 3 (CEx. 3) and the inventive examples 5 and 6 (Ex. 5 and 6) included 13 wt % of ethylbenzene, 1.5 wt % of C8-C9 non-aromatics, 1.5 wt % of para-xylene, 19 wt % of ortho-xylene, and 66 wt % of meta-xylene. In all examples, the catalysts used were in the form of comparably sized extrudates that included the ZSM-5 zeolite or the ZSM-11 zeolite and a silica binder.

The extrudates were dried under flowing nitrogen gas, ramping at a temperature of 7° C. per minute from room temperature to 200° C. and held at 200° C. for sixteen hours. The extrudates were then heated from 200° C. to 360° C., ramping at a rate of 7° C. per minute. The extrudates were held at 360° C. for four hours. The extrudates were cooled at a rate of 23° C. per minute until the temperature reached 330° C. Upon reaching the temperature of 330° C., the extrudates were contacted with the para-xylene depleted xylenes feed in the presence of hydrogen. The isomerization conditions were set to 1.55 MPag with a molecular hydrogen to hydrocarbon molar ratio of 1, while the WHSV was varied from 12 $hr^{-1}$ to 48 $hr^{-1}$ and the temperature was varied from 330° C. to 365° C. The process conditions and isomerization results are shown in Tables 1-3 below. In the tables, H2:HC means molecular hydrogen to hydrocarbon ratio, MPag means mega-pascal gauge pressure.

Comparative Example 3 (CEx. 3)

A 1 gram sample of the extrudate from Comparative Example 2 was packed in a tubular reactor.

TABLE 1

CEx. 3 - ZSM-5 Zeolite for Xylenes Isomerization

| | | | | | |
|---|---|---|---|---|---|
| Pressure, MPag | 1.55 | 1.55 | 1.55 | 1.55 | 1.55 |
| $H_2$:HC, molar ratio | 1 | 1 | 1 | 1 | 1 |
| WHSV, $hr^{-1}$ | 12 | 24 | 36 | 36 | 36 |
| Temperature, °C. | 365 | 365 | 365 | 345 | 330 |
| pX selectivity in product, % | 24 | 23.8 | 23.6 | 23.5 | 23.3 |
| Ethylbenzene conversion, % | 83.2 | 70.5 | 61.6 | 43.2 | 29.7 |
| Benzene Yield, wt % | 5.07 | 3.3 | 2.36 | 1.6 | 1 |
| Toluene yield, wt % | 13.3 | 7.4 | 4.6 | 2.2 | 1.2 |
| Trimethylbenzenes yield, wt % | 7.1 | 4.7 | 3.4 | 1.7 | 0.9 |
| Xylenes Loss, % | 24.8 | 15.9 | 11.2 | 5.7 | 2.6 |

Example 5 (Ex. 5)

A 1 gram sample of the extrudate from Example 3 was packed in a tubular reactor.

TABLE 2

Ex. 5 - ZSM-11 Zeolite for Xylenes Isomerization

| | | | | | |
|---|---|---|---|---|---|
| Pressure, MPag | 1.55 | 1.55 | 1.55 | 1.55 | 1.55 |
| $H_2$:HC, molar ratio | 1 | 1 | 1 | 1 | 1 |
| WHSV, $hr^{-1}$ | 12 | 24 | 36 | 36 | 36 |
| Temperature, °C. | 365 | 365 | 365 | 345 | 330 |
| pX selectivity in product, % | 24 | 23.9 | 23.7 | 23.75 | 23.5 |
| Ethylbenzene conversion, % | 74.6 | 61.1 | 52.1 | 33.9 | 21.6 |
| Benzene Yield, wt % | 4.6 | 3.1 | 2.2 | 1.3 | 0.8 |
| Toluene Yield, wt % | 7.9 | 4.1 | 2.5 | 1 | 0.5 |
| Trimethylbenzenes Yield, wt % | 4.2 | 2.5 | 1.8 | 0.8 | 0.4 |
| Xylenes Loss, % | 17.2 | 10.4 | 7.4 | 3.2 | 1 |

The ideal metric for selectivity is the trimethylbenzenes yield that is predominantly formed by xylenes transalkylation. This represents a pathway for xylenes loss that is more representative for a typical bottom bed catalyst in a dual-bed system, as ethylbenzene is primarily converted in the top bed and xylenes isomerization is primarily carried out in the second bed. As such, a reduction in the production of trimethylbenzenes suggests that xylene transalkylation is disfavored and should represent an improved yield for dual bed xylenes isomerization processes. As can be seen, when compared with CEx. 3, the trimethylbenzenes yield for Ex. 5 was lower at comparable ethylbenzene conversion rates.

Example 6 (Ex. 6)

A 1 gram sample of the extrudate from Example 4 was packed in a tubular reactor.

TABLE 3

Ex. 6 - ZSM-11 Zeolite for Xylenes Isomerization

| | | | | | | |
|---|---|---|---|---|---|---|
| Pressure, MPag | 1.55 | 1.55 | 1.55 | 1.55 | 1.55 | 1.55 |
| $H_2$:HC, molar ratio | 1 | 1 | 1 | 1 | 1 | 1 |
| WHSV, $hr^{-1}$ | 12 | 24 | 36 | 36 | 36 | 48 |
| Temperature, °C. | 365 | 365 | 365 | 345 | 330 | 330 |
| pX selectivity in product, % | 23.9 | 23.3 | 22.6 | 21.7 | 21 | 20.2 |
| Ethylbenzene conversion, % | 47.1 | 36.1 | 30.6 | 17.5 | 10.4 | 9.1 |
| Benzene Yield, wt % | 3.2 | 2 | 1.4 | 0.4 | 0 | 0 |
| Toluene Yield, wt % | 2.3 | 1.1 | 0.6 | 0.2 | 0 | 0 |
| Trimethylbenzenes Yield, wt % | 1.4 | 0.8 | 0.5 | 0.2 | 0.1 | 0.1 |
| Xylenes Loss, % | 6.7 | 4.6 | 3.8 | 1.7 | 0.5 | 0.4 |

As can be seen, when compared with CEx. 3, the trimethylbenzenes yield for Ex. 6 was lower at comparable ethylbenzene conversion rates.

Dual Catalyst Bed System Example

To demonstrate the performance of ZSM-11 zeolite as a bottom bed catalyst in a downflow reactor, the ZSM-11 zeolite was tested in a dual-bed system and compared to the ZSM-5 zeolite in a substantially similar configuration. In the comparative example (CEx. 4), the first bed included 1 g of the ZSM-5 zeolite and the second bed included 3 g of the ZSM-5 zeolite. In the inventive example (Ex. 7), the first bed included 1 g of the same ZSM-5 zeolite used in CEx. 4, but only 1 g of the ZSM-11 zeolite of Ex. 4 in the second bed. The gaseous hydrocarbon feed used in the CEx. 4 and Ex. 7 included 13 wt % of ethylbenzene, 1 wt % of C8-C9 non-aromatics, 1 wt % of para-xylene, 19 wt % of ortho-xylene, and 66 wt % of meta-xylene. As in the single-bed system examples, the catalysts used were in the form of comparably sized extrudates that included the ZSM-5 zeolite or the ZSM-11 zeolite and a silica binder.

The extrudates were dried under flowing nitrogen gas, ramping at 7° C. per minute from room temperature to 200° C. and held at 200° C. for sixteen hours. The extrudates were then heated from 200° C. to 360° C., ramping at a rate of 7° C. per minute. The extrudates were held at 360° C. for four hours. The extrudates were cooled at a rate of 23° C. per minute until the temperature reached 330° C. Afterward, the extrudates were contacted with the gaseous hydrocarbon feed in the presence of hydrogen. Results, as shown in Table 4, demonstrate the isomerization of the gaseous hydrocarbon feed.

TABLE 4

Dual Bed System

| | CEx. 4 | Ex. 7 |
|---|---|---|
| First Catalyst Bed | ZSM-5, 1 g | ZSM-5, 1 g |
| Second Catalyst Bed | ZSM-5, 3 g | ZSM-11, 1 g (of Ex. 4) |
| Pressure, MPag | 1.55 | 1.55 |
| $H_2$:Oil, molar ratio | 1 | 1 |
| WHSV, $hr^{-1}$ | 12 | 24 |
| Temperature, ° C. | 368 | 372 |
| pX selectivity in product, wt % | 23.5 | 23.9 |
| EB Conv., % | 74.5 | 75.8 |
| Benzene Yield, wt % | 5.7 | 6 |
| Toluene Yield, wt % | 1.7 | 1.6 |
| Trimethylbenzenes Yield, wt % | 0.4 | 0.4 |
| Xylenes Loss, wt % | 4.2 | 3.7 |

As can be seen by comparing Ex. 7 and CEx. 4, the pX selectivity in the products and the ethylbenzene conversions are comparable despite that Ex. 7 used only one third of the catalyst in the second bed and was operated at double the WHSV as compared to CEx. 4. Additionally, the xylene losses decreased and the benzene yield increased. The reduced amount of the second catalyst and the increased WHSV while also reducing xylene loses were surprising and unexpected.

LISTING OF EMBODIMENTS

This disclosure may further include the following non-limiting embodiments.

A1. A process for converting C8 aromatic hydrocarbons, comprising: (I) feeding a gaseous hydrocarbon feed comprising meta-xylene, ortho-xylene, or both into a conversion zone; and (II) contacting the gaseous hydrocarbon feed with a catalyst comprising a ZSM-11 zeolite in the conversion zone under conversion conditions to effect isomerization of at least a portion of any meta-xylene, at least a portion of any ortho-xylene, or both to produce a conversion product rich in para-xylene, wherein the ZSM-11 zeolite has an alpha value of 1 to 3,000 and a silica to alumina molar ratio of from 15 to 200.

A2. The process of A1, wherein the catalyst further comprises a ZSM-5 zeolite.

A3. The process of A1 or A2, wherein the catalyst comprises a ZSM-5/ZSM-11 intergrowth zeolite.

A4. The process of A1 to A3, wherein the catalyst comprises from 1 wt % to 100 wt % of the ZSM-11 zeolite, based on a total weight of all zeolites present in the catalyst.

A5. The process of A1 to A4, wherein the ZSM-11 zeolite has an alpha value of from 20 to 2,000.

A6. The process of A1 to A5, wherein the ZSM-11 zeolite has a molar ratio of silica to alumina from 20 to 100.

A7. The process of A1 to A6, wherein the ZSM-11 zeolite has a micropore surface area of from 100 $m^2/g$ to 600 $m^2/g$ and an external surface area of from 20 $m^2/g$ to 250 $m^2/g$.

A8. The process of A1 to A7, wherein: the ZSM-11 zeolite has a micropore surface area of from 100 $m^2/g$ to 600 $m^2/g$ and an external surface area of from 20 $m^2/g$ to 250 $m^2/g$, the catalyst is an extrudate comprising the ZSM-11 zeolite and a binder, and the extrudate has a micropore surface area of from 50 $m^2/g$ to 600 $m^2/g$ and an external surface area of from 30 $m^2/g$ to 400 $m^2/g$.

A9. The process of A1 to A8, wherein: the conversion conditions comprise a temperature of 200° C. to 600° C. and a weight hour space velocity of from 12 $hour^{-1}$ to 48 $hour^{-1}$, the process exhibits a xylenes loss (Lx(1)) that is ≥25% less as compared to a xylenes loss (Lx(2)) of a comparative process operated under a comparable ethylbenzene conversion and a comparable para-xylene selectivity such that Lx(1) is ≤0.75×Lx(2), wherein the comparable ethylbenzene conversion is within 10 percentage points or less of an ethylbenzene conversion of the process and the comparable para-xylene selectivity is within 2 percent of a para-xylene selectivity of the process, the comparative process uses a comparative catalyst that is a comparative extrudate comprising a ZSM-5 zeolite having an alpha value of 1 to 3000, a silica to alumina molar ratio of from 15 to 200, a micropore surface area of from 50 $m^2/g$ to 600 $m^2/g$ and an external surface area of from 30 $m^2/g$ to 400 $m^2/g$, and the comparative extrudate has a micropore surface area of from 50 $m^2/g$ to 600 $m^2/g$ and an external surface area of from 30 $m^2/g$ to 400 $m^2/g$.

A10. The process of A1 to A9, wherein: the ZSM-11 zeolite has a micropore surface area of from 250 $m^2/g$ to 500 $m^2/g$ or 300 $m^2/g$ to 500 $m^2/g$ and an external surface area of from 100 $m^2/g$ to 200 $m^2/g$ or 100 $m^2/g$ to 150 $m^2/g$, the catalyst is an extrudate comprising the ZSM-11 zeolite and a binder, and the extrudate has a micropore surface area of from 100 $m^2/g$ to 450 $m^2/g$ or 150 $m^2/g$ to 300 $m^2/g$ and an external surface area of from 50 $m^2/g$ to 400 $m^2/g$ or 100 $m^2/g$ to 300 $m^2/g$.

A11. The process of A1 to A10, wherein the ZSM-11 zeolite is in the form of crystals having a size of 10 nm to 1 μm, or 15 nm to 0.5 μm, or 20 nm to 100 nm, or <100 nm, or <50 nm.

A12. The process of A1 to A11, wherein the ZSM-11 zeolite is the form of crystals having non-needle and non-fiber morphology, and wherein the crystals have a length to diameter ratio of <5, <4, or <3.

A13. The process of A1 to A12, wherein: the catalyst is an extrudate comprising the ZSM-11 zeolite and a binder, the binder comprises silica, alumina, or a mixture thereof, and the extrudate comprises about 0.1 wt % to about 95 wt % of the binder based on the combined weight of the ZSM-11 zeolite and the binder.

A14. The process of A1 to A13, wherein: the ZSM-11 zeolite has a micropore surface area of from 300 $m^2/g$ to 500 $m^2/g$ and an external surface area of from 100 $m^2/g$ to 150 $m^2/g$, the catalyst is an extrudate comprising the ZSM-11 zeolite and a binder, the binder comprises silica, and the extrudate has a micropore surface area of from 150 $m^2/g$ to 300 $m^2/g$ and an external surface area of from 100 $m^2/g$ to 300 $m^2/g$.

A15. The process of A1 to A14, wherein: the ZSM-11 zeolite has an alpha value of from 50 to 500, the ZSM-11 zeolite has a molar ratio of silica to alumina is from 20 to 50, the ZSM-11 zeolite has a micropore surface area of from 300 $m^2/g$ to 500 $m^2/g$ and an external surface area of from 100 $m^2/g$ to 150 $m^2/g$, the catalyst is an extrudate comprising the ZSM-11 zeolite and a binder, the binder comprises alumina, silica, or a mixture thereof, the extrudate comprises about 0.1 wt % to about 95 wt % of the binder based on the combined weight of the ZSM-11 zeolite and the binder, and the extrudate has a micropore surface area of from 150 $m^2/g$ to 300 $m^2/g$ and an external surface area of from 100 $m^2/g$ to 300 $m^2/g$.

A16. The process of A1 to A15, wherein the feed contacts the catalyst at a weight hour space velocity of from 0.1 hour$^{-1}$ to 60 hour$^{-1}$, and wherein the conversion conditions comprise a temperature of from 200° C. to 600° C.

A17. The process of A1 to A16, wherein the gaseous hydrocarbon feed is contacted with the catalyst in the conversion zone in the presence of molecular hydrogen, and wherein a molar ratio of the molecular hydrogen to hydrocarbons in the gaseous hydrocarbon feed is from 0.01 to 2.

B1. A process for converting C8 aromatic hydrocarbons, comprising: (I) feeding a gaseous hydrocarbon feed comprising ethylbenzene and at least one of ortho-xylene and meta-xylene into a first conversion zone; (II) contacting the gaseous hydrocarbon feed with a first catalyst in the first conversion zone under first conversion conditions to effect conversion of at least a portion of the ethylbenzene into benzene and ethane to produce a gaseous effluent lean in ethylbenzene; (III) feeding the gaseous effluent into a second conversion zone; and (IV) contacting the gaseous effluent with a second catalyst comprising a ZSM-11 zeolite within the second conversion zone under second conversion conditions to effect isomerization of at least a portion of any ortho-xylene, at least a portion of any meta-xylene, or both to para-xylene to produce a conversion product rich in para-xylene, wherein the ZSM-11 zeolite has an alpha value of 1 to 5,000 and a silica to alumina molar ratio of from 15 to 200.

B2. The process of B1, wherein the second catalyst further comprises a ZSM-5 zeolite.

B3. The process of B1 or B2, wherein the first catalyst comprises a ZSM-5 zeolite, a ZSM-11 zeolite, a ZSM-5/ZSM-11 intergrowth zeolite, or a mixture thereof.

B4. The process of B1 to B3, wherein: the ZSM-11 zeolite has a micropore surface area of from 100 m$^2$/g to 600 m$^2$/g and an external surface area of from 20 m$^2$/g to 250 m$^2$/g, the second catalyst is an extrudate comprising the ZSM-11 zeolite and a binder, the binder comprises alumina, silica, or a mixture thereof, and the extrudate has a micropore surface area of from 50 m$^2$/g to 600 m$^2$/g and an external surface area of from 30 m$^2$/g to 400 m$^2$/g.

B5. The process of B4, wherein: the second conversion conditions comprise a temperature of from 200° C. to 600° C. and a weight hour space velocity of from 12 hour$^{-1}$ to 48 hour$^{-1}$, the process exhibits a xylenes loss (Lx(1)) that is ≥25% less as compared to a xylenes loss (Lx(2)) of a comparative process operated under a comparable ethylbenzene conversion and a comparable para-xylene selectivity such that Lx(1) is ≤0.75×Lx(2), wherein the comparable ethylbenzene conversion is within 10 percentage points or less of an ethylbenzene conversion of the process and the comparable para-xylene selectivity is within 2 percent of a para-xylene selectivity of the process, the comparative process uses a comparative catalyst that is a comparative extrudate comprising a ZSM-5 zeolite having an alpha value of 1 to 3000, a silica to alumina molar ratio of from 15 to 200, a micropore surface area of from 50 m$^2$/g to 600 m$^2$/g, and an external surface area of from 20 m$^2$/g to 250 m$^2$/g, and the comparative extrudate has a micropore surface area of from 50 m$^2$/g to 600 m$^2$/g and an external surface area of from 30 m$^2$/g to 400 m$^2$/g.

B6. The process of B1 to B5, wherein: the ZSM-11 zeolite has an alpha value of from 50 to 500, the ZSM-11 zeolite has a molar ratio of silica to alumina from 20 to 50, the ZSM-11 zeolite has a micropore surface area of from 250 m$^2$/g to 500 m$^2$/g and an external surface area of from 100 m$^2$/g to 250 m$^2$/g, the second catalyst is an extrudate comprising the ZSM-11 zeolite and a binder, the binder comprises alumina, silica, or a mixture thereof, the extrudate has a micropore surface area of from 100 m$^2$/g to 450 m$^2$/g and an external surface area of from 50 m$^2$/g to 400 m$^2$/g, and the extrudate comprises about 0.1 wt % to about 95 wt % of the binder based on the combined weight of the ZSM-11 zeolite and the binder.

B7. The process of B1 to B6, wherein the gaseous aromatic hydrocarbon feed further comprises molecular hydrogen, and wherein a molar ratio of the molecular hydrogen to hydrocarbons in the gaseous hydrocarbon feed is from 0.01 to 2.

B8. The process of B1 to B7, wherein the first catalyst comprises a ZSM-5 zeolite, and wherein a weight ratio of the ZSM-5 zeolite in the first catalyst to the ZSM-11 zeolite in the second catalyst is ≥1.5.

B9. The process of B1 to B8, wherein the first conversion zone conditions and the second conversion zone conditions comprise a temperature of from 200° C. to 600° C. and a weight hour space velocity of from 0.1 hour$^{-1}$ to 60 hour$^{-1}$.

B10. The process of B1 to B9, wherein the ZSM-11 zeolite is in the form of crystals having a size of 10 nm to 1 μm, or 15 nm to 0.5 μm, or 20 nm to 100 nm, or <100 nm, or <50 nm.

B11. The process of B1 to B10, wherein the ZSM-11 zeolite is the form of crystals having non-needle and non-fiber morphology, and wherein the crystals have a length to diameter ratio of <5, <4, or <3.

B12. The process of B1 to B11, wherein the first catalyst comprises a ZSM-5/ZSM-11 intergrowth zeolite.

B13. The process of B1 to B12, wherein the second catalyst comprises a ZSM-5/ZSM-11 intergrowth zeolite.

B14. The process of B1 to B13, wherein the first catalyst is a selectivated first catalyst.

B15. The process of B14, wherein the first catalyst is subjected to a silica selectivation treatment process, a coke selectivation treatment process, or a combination thereof to produce the selectivated first catalyst.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for converting C8 aromatic hydrocarbons, comprising:
   (I) feeding a gaseous hydrocarbon feed comprising meta-xylene, ortho-xylene, or both into a conversion zone; and
   (II) contacting the gaseous hydrocarbon feed with a catalyst comprising a ZSM-11 zeolite in the conversion zone under conversion conditions to effect isomerization of at least a portion of any meta-xylene, at least a portion of any ortho-xylene, or both to produce a conversion product n comprising para-xylene, wherein the ZSM-11 zeolite has an alpha value of 1 to 3,000, a total surface area of less than 500 m$^2$/g, and a molar ratio of silica to alumina of from 25 to 50.

2. The process of claim 1, wherein the catalyst further comprises a ZSM-5 zeolite.

3. The process of claim 1, wherein the catalyst comprises a ZSM-5/ZSM-11 intergrowth zeolite.

4. The process of claim 1, wherein the catalyst comprises from 1 wt % to 100 wt % of the ZSM-11 zeolite, based on a total weight of all zeolites present in the catalyst.

5. The process of claim 1, wherein the ZSM-11 zeolite has an alpha value of from 20 to 2,000.

6. The process of claim 1, wherein the ZSM-11 zeolite has a micropore surface area of from 100 m$^2$/g to 600 m$^2$/g and an external surface area of from 20 m$^2$/g to 250 m$^2$/g.

7. The process of claim 6, wherein:
the catalyst is an extrudate comprising the ZSM-11 zeolite and a binder, and
the extrudate has a micropore surface area of from 50 m$^2$/g to 600 m$^2$/g and an external surface area of from 30 m$^2$/g to 400 m$^2$/g.

8. The process of claim 7, wherein:
the conversion conditions comprise a temperature of from 200° C. to 600° C. and a weight hour space velocity of from 12 hour$^{-1}$ to 48 hour$^{-1}$,
the process exhibits a xylenes loss (Lx(1)) that is ≥25% less as compared to a xylenes loss (Lx(2)) of a comparative process operated under a comparable ethylbenzene conversion and a comparable para-xylene selectivity such that Lx(1) is ≤0.75×Lx(2), wherein the comparable ethylbenzene conversion is within 10 percentage points or less of an ethylbenzene conversion of the process and the comparable para-xylene selectivity is within 2 percent of a para-xylene selectivity of the process,
the comparative process uses a comparative catalyst that is a comparative extrudate comprising a ZSM-5 zeolite having an alpha value of 1 to 3000, a micropore surface area of from 50 m$^2$/g to 600 m$^2$/g and an external surface area of from 30 m$^2$/g to 400 m$^2$/g, and
the comparative extrudate has a micropore surface area of from 50 m$^2$/g to 600 m$^2$/g and an external surface area of from 30 m$^2$/g to 400 m$^2$/g.

9. The process of claim 1, wherein:
the ZSM-11 zeolite has a micropore surface area of from 250 m$^2$/g to 500 m$^2$/g and an external surface area of from 100 m$^2$/g to 200 m$^2$/g,
the catalyst is an extrudate comprising the ZSM-11 zeolite and a binder, and
the extrudate has a micropore surface area of from 100 m$^2$/g to 450 m$^2$/g and an external surface area of from 50 m$^2$/g to 400 m$^2$/g.

10. The process of claim 1, wherein the ZSM-11 zeolite is in the form of crystals having a crystallite size of 1 μm to 0.05 μm.

11. The process of claim 1, wherein the ZSM-11 zeolite is the form of crystals having non-needle and non-fiber morphology, and wherein the crystals have a length to diameter ratio of <5.

12. The process of claim 1, wherein:
the catalyst is an extrudate comprising the ZSM-11 zeolite and a binder,
the binder comprises silica, alumina, or a mixture thereof, and
the extrudate comprises about 0.1 wt % to about 95 wt % of the binder based on the combined weight of the ZSM-11 zeolite and the binder.

13. The process of claim 1, wherein:
the ZSM-11 zeolite has a micropore surface area of from 300 m$^2$/g to 500 m$^2$/g and an external surface area of from 100 m$^2$/g to 150 m$^2$/g,
the catalyst is an extrudate comprising the ZSM-11 zeolite and a binder,
the binder comprises silica, and
the extrudate has a micropore surface area of from 150 m$^2$/g to 300 m$^2$/g and an external surface area of from 100 m$^2$/g to 300 m$^2$/g.

14. The process of claim 1, wherein:
the ZSM-11 zeolite has an alpha value of from 50 to 500,
the ZSM-11 zeolite has a micropore surface area of from 300 m$^2$/g to 500 m$^2$/g and an external surface area of from 100 m$^2$/g to 150 m$^2$/g,
the catalyst is an extrudate comprising the ZSM-11 zeolite and a binder,
the binder comprises alumina, silica, or a mixture thereof,
the extrudate comprises about 0.1 wt % to about 95 wt % of the binder based on the combined weight of the ZSM-11 zeolite and the binder, and
the extrudate has a micropore surface area of from 150 m$^2$/g to 300 m$^2$/g and an external surface area of from 100 m$^2$/g to 300 m$^2$/g.

15. The process of claim 1, wherein the feed contacts the catalyst at a weight hour space velocity of from 0.1 hour-1 to 60 hour$^{-1}$, and wherein the conversion conditions comprise a temperature of from 200° C. to 600° C.

16. The process of claim 1, wherein the gaseous hydrocarbon feed is contacted with the catalyst in the conversion zone in the presence of molecular hydrogen, and wherein a molar ratio of the molecular hydrogen to hydrocarbons in the gaseous hydrocarbon feed is from 0.01 to 2.

* * * * *